US009316645B2

(12) United States Patent
Rose-Petruck et al.

(10) Patent No.: US 9,316,645 B2
(45) Date of Patent: Apr. 19, 2016

(54) METHODS, COMPOSITIONS AND KITS FOR IMAGING CELLS AND TISSUES USING NANOPARTICLES AND SPATIAL FREQUENCY HETERODYNE IMAGING

(71) Applicant: Brown University, Providence, RI (US)

(72) Inventors: Christoph Rose-Petruck, Barrington, RI (US); Jack R. Wands, East Greenwich, RI (US); Danielle Rand, Quincy, MA (US); Zoltan Derdak, Riverside, RI (US); Vivian Ortiz, Nashville, TN (US)

(73) Assignees: BROWN UNIVERSITY, Providence, RI (US); RHODE ISLAND HOSPITAL, Providence, RI (US)

( * ) Notice: Subject to any disclaimer, the term of this patent is extended or adjusted under 35 U.S.C. 154(b) by 0 days.

(21) Appl. No.: 13/645,938

(22) Filed: Oct. 5, 2012

(65) Prior Publication Data

US 2013/0095499 A1    Apr. 18, 2013

Related U.S. Application Data

(60) Provisional application No. 61/544,419, filed on Oct. 7, 2011, provisional application No. 61/546,484, filed on Oct. 12, 2011.

(51) Int. Cl.
| | | |
|---|---|---|
| G01N 33/574 | (2006.01) | |
| G01N 33/569 | (2006.01) | |
| A61K 49/04 | (2006.01) | |
| B82Y 5/00 | (2011.01) | |

(52) U.S. Cl.
CPC ...... *G01N 33/57438* (2013.01); *A61K 49/0428* (2013.01); *B82Y 5/00* (2013.01); *G01N 33/56966* (2013.01); *G01N 33/57484* (2013.01); *G01N 2500/00* (2013.01)

(58) Field of Classification Search
None
See application file for complete search history.

(56) References Cited

U.S. PATENT DOCUMENTS

| | | | | |
|---|---|---|---|---|
| 5,111,495 | A * | 5/1992 | Miklavcic | ..................... 378/146 |
| 5,212,085 | A | 5/1993 | Wands et al. | |
| 5,314,679 | A * | 5/1994 | Lewis et al. | ................. 424/9.322 |
| 5,505,932 | A | 4/1996 | Grinstaff et al. | |
| 5,811,077 | A | 9/1998 | Seri et al. | |
| 5,902,795 | A | 5/1999 | Toole et al. | |
| 6,370,415 | B1 | 4/2002 | Weiler et al. | |
| 6,529,582 | B2 | 3/2003 | Feldmesser et al. | |
| 6,595,211 | B2 | 7/2003 | Weiler et al. | |
| 6,707,884 | B1 | 3/2004 | Ogawa | |
| 6,797,696 | B2 | 9/2004 | Wands et al. | |
| 6,955,639 | B2 * | 10/2005 | Hainfeld et al. | ................... 600/1 |
| 7,985,398 | B2 | 7/2011 | Brooks et al. | |
| 7,985,426 | B1 | 7/2011 | Sung et al. | |
| 7,988,761 | B2 | 8/2011 | Jun et al. | |
| 8,227,022 | B2 | 7/2012 | Magdassi et al. | |
| 8,231,369 | B2 | 7/2012 | Rajala et al. | |
| 8,241,922 | B2 | 8/2012 | Murphy et al. | |
| 8,263,035 | B2 | 9/2012 | Davis et al. | |
| 2005/0123545 | A1 * | 6/2005 | Wands et al. | ............... 424/146.1 |
| 2005/0267069 | A1 | 12/2005 | Brown et al. | |
| 2008/0050592 | A1 | 2/2008 | Fiannaca et al. | |
| 2010/0092384 | A1 * | 4/2010 | Bumb et al. | .................. 424/1.29 |

FOREIGN PATENT DOCUMENTS

| | | | | |
|---|---|---|---|---|
| EP | 0338841 | B1 | 3/1995 | |
| WO | 8704462 | A1 | 7/1987 | |
| WO | 8901036 | A1 | 2/1989 | |
| WO | WO 2009049083 | A1 * | 4/2009 | ............ A61B 5/055 |

OTHER PUBLICATIONS

Bennett et al., A grating-based single-shot x-ray phase contrast and diffraction method for in vivo imaging, Med. Phys. 37 (11), 2010, 6047-6054.*
Stein et al., Selective imaging of nano-particle contrast agents by a single-shot x-ray diffraction technique, Optics Express, 18(12), 13271-13278, 2010.*
Alexis et al. "Factors affecting the clearance and biodistribution of polymeric nanoparticles" Mol Pharm, 2008, vol. 5, pp. 505-515.
Brandenberger et al. "Quantitative evaluation of cellular uptake and trafficking of plain and polyethylene glycol-coated gold nanoparticles" Small, 2010, vol. 6, pp. 1669-1678.
Bruix et al. "New aspects of diagnosis and therapy of hepatocellular carcinoma" Oncogene, 2006, vol. 25, pp. 3848-3856.
Choi et al. "A cellular trojan horse for delivery of therapeutic nanoparticles into tumors" Nano Lett, 2007, vol. 7, pp. 3759-3765.
Colombo "Hepatocellular carcinoma" J Hepatol, 1992, vol. 15, pp. 225-236.
El-Sarag et al. "Rising incidence of hepatocellular carcinoma in the United States" N Engl J Med, 1999, vol. 340, pp. 745-750.
Gittins et al. "Tailoring the polyelectrolyte coating of metal nanoparticles"J Phys Chem, 2001, vol. 105, pp. 6846-6852.
Gole et al. "Polyelectrolyte-coated gold nanorods: synthesis, characterization and immobilization" Chem Mater, 2005, vol. 17, pp. 1325-1330.
Hain et al. "Recent advances in imaging hepatocellular carcinoma: diagnosis, staging and response assessment: functional imaging" Cancer J, 2004, vol. 10, pp. 121-127.

(Continued)

*Primary Examiner* — Galina Yakovleva
*Assistant Examiner* — Andrea S Grossman
(74) *Attorney, Agent, or Firm* — Lawson & Weitzen LLP; Sonia K. Guterman; Michael I. Falkoff

(57) ABSTRACT

Methods, compositions, systems, devices and kits are provided herein for preparing and using a nanoparticle composition and spatial frequency heterodyne imaging for visualizing cells or tissues. In various embodiments, the nanoparticle composition includes at least one of: a nanoparticle, a polymer layer, and a binding agent, such that the polymer layer coats the nanoparticle and is for example a polyethylene glycol, a polyelectrolyte, an anionic polymer, or a cationic polymer, and such that the binding agent that specifically binds the cells or the tissue. Methods, compositions, systems, devices and kits are provided for identifying potential therapeutic agents in a model using the nanoparticle composition and spatial frequency heterodyne imaging.

16 Claims, 5 Drawing Sheets

(56) References Cited

OTHER PUBLICATIONS

Hainfeld et al. "The use of gold nanoparticles to enhance radiotherapy in mice" Phys Med Biol, 2004, vol. 49, pp. N309-N315.
Hainfeld et al. "Gold nanoparticles: a new x-ray contrast agent" Br J Radiol, 2006, vol. 79, pp. 248-253.
Harada et al. "Monoclonal antibody G6k12 specific for membrane-associated differentiation marker of human stratified squamous epithelia and squamous cell carcinoma" J Oral Pathol Med, 1993, vol. 22, pp. 145-152.
He et al. "Establishment and characterization of a new human hepatocellular carcinoma cell line" In Vitro, 1984, vol. 20, pp. 493-504.
Hirsch et al. "Nanoshell-mediated near-infrared thermal therapy of tumors under magnetic resonance guidance" Proc Natl Acad Sci USA, 2003, vol. 100, pp. 13549-13554.
Hucknall et al. "In pursuit of zero: polymer brushes that resist the adsorption of proteins" Advanced Materials, 2009, vol. 21, pp. 2441-2446.
Hurwitz et al. "A conjugate of 5-fluorouridine-poly(L-lysine) and an antibody reactive with human colon carcinoma" Bioconjug Chem, 1990, vol. 1, pp. 285-290.
Inai et al. "Immunohistochemical detection of an enamel protein-related epitope in rat bone at an early stage of osteogenesis" Histochemistry, 1993, vol. 99, pp. 355-362.
Kaufman et al. "Amplification and expression of sequences cotransfected with a modular dihydrofolate reductase complementary DNA gene" J Mol Biol, 1982, vol. 159, pp. 601-621.
Kim et al. "Antibiofouling polymer-coated gold nanoparticles as a contrast agent for in vivo x-ray computed tomography imaging" J Am Chem Soc, 2007, vol. 129, pp. 7661-7665.
Kojima et al. "X-ray computed tomography contrast agents prepared by seeded growth of gold nanoparticles in PEGylated dendrimer" Nanotechnol, 2010, vol. 21, p. 245104 (6 pp).
Lal et al. "Nanoshell-enabled photothermal cancer therapy: impending clinical impact" Acc Chem Res, 2008, vol. 12, pp. 1842-1851.
Lee et al. "Blood compatibility of polyethylene oxide surfaces" Prog Polym Sci, 1995, vol. 20, pp. 1043-1079.
Lipka et al. "Biodistribution of PEG-modified gold nanoparticles following intratracheal instillation and intravenous injection" Biomaterials, 2010, vol. 31, pp. 6574-6581.
Luu et al. "Prognostic value of aspartyl (asparaginyl)-β-hydroxylase/humbug expression in non-small cell lung carcinoma" Hum Pathol, 2009, vol. 40, pp. 639-644.
Mayya et al. "Preparation and organization of nanoscale polyelectrolyte-coated gold nanoparticles" 2003, Adv Funct Mater, vol. 13, pp. 183-188.
Mendelsohn et al. "Rational design of cytophilic and cytophobic polyelectrolyte multilayer thin films" Biomacromolecules, 2003, vol. 4, pp. 96-106.
Mulder et al. "Characterization of two human monoclonal antibodies reactive with Hla-B12 and Hla-B60, respectively, raised by in vitro secondary immunization of peripheral blood lymphocytes" Hum Pathol, 1993, vol. 36, pp. 186-192.
O'Brien et al. "Hepatocellular carcinoma: paradigm of preventive oncology" Cancer J, 2004, vol. 10, pp. 67-73.
Okuda "Hepatocellular carcinoma" J Hepatol, 2000, vol. 32, pp. 225-237.
Rand et al. "Nanomaterials for x-ray imaging: gold nanoparticle enhancement of x-ray scatter imaging of hepatocellular carcinoma" Nano Lett, 2011, vol. 11, pp. 2678-2683.
Sheu et al. "Early detection of hepatocellular carcinoma by real-time ultrasonography" Cancer, 1985, vol. 56, pp. 660-666.
Shiratori et al. "pH-dependent thickness behavior of sequentially adsorbed layers of weak polyelectrolytes" Macromolecules, 2000, vol. 33, pp. 4213-4219.
Stäuber et al. "Rapid generation of monoclonal antibody-secreting hybridomas against African horse sickness virus by in vitro immunization and the fusion/cloning technique" J Immunol Methods, 1993, vol. 161, pp. 157-168.
Stein et al. "Selective imaging of nano-particle contrast agents by a single-shot x-ray diffraction technique" Opt Express, 2010, vol. 18, pp. 13271-13278.
Takahashi et al. "In vivo localization of human colon adenocarcinoma by monoclonal antibody binding to a highly expressed cell surface antigen" Cancer Res, 1988, vol. 48, pp. 6573-6579.
Takahashi et al. "Radioimmunolocation of hepatic and pulmonary metastasis of human colon adenocarcinoma" Gastroenterol, 1989, vol. 96, pp. 1317-1329.
Trevisani et al. "Recent advances in the natural history of hepatocellular carcinoma" Carcinogenesis, 2008, vol. 29, pp. 1299-1305.
Urlaub et al. "Isolation of Chinese hamster cell mutants deficient in dihydrofolate reductase activity" Proc Natl Acad Sci USA, 1980, vol. 77, pp. 4216-4220.
Venkateswaran et al. "Production of anti-fibroblast growth factor receptor monoclonal antibodies by in vitro immunization" Hybridoma, 1992, vol. 11, pp. 729-739.
Wen et al. "Spatial harmonic imaging of x-ray scattering—initial results" IEEE Trans Med Imag, 2008, vol. 27, pp. 997-1002.
Wen et al. "Fourier x-ray scattering radiography yields bone structural information" Radiology, 2009, vol. 251, pp. 910-918.
Yang et al. "Vapor phase synthesis of supported Pd, Au, and unsupported bimetallic nanoparticle catalysts for CO oxidation" Catal Commun, 2006, vol. 7, pp. 281-284.
Yang et al. "Theoretical variance analysis of single- and dual-energy computed tomography methods for calculating proton stopping power ratios of biological tissues" Phys Med Biol, 2010, vol. 55, pp. 1343-1362.

\* cited by examiner

METHODS, COMPOSITIONS AND KITS FOR IMAGING CELLS AND TISSUES USING NANOPARTICLES AND SPATIAL FREQUENCY HETERODYNE IMAGING

RELATED APPLICATIONS

The present application claims the benefit of U.S. provisional application Ser. Nos. 61/544,419 filed Oct. 7, 2011 and 61/546,484 filed Oct. 12, 2011 in the U.S. Patent and Trademark Office, and which are incorporated herein by reference in their entireties.

GOVERNMENT FUNDING

A portion of this work was supported by U.S. Department of Energy grant DE-FG02-08ER15937, U.S. Department of Education GAANN award P200A090076, and the National Institutes of Health grant CA123544. The government has certain rights in this invention.

TECHNICAL FIELD

Systems, compositions, methods and kits are provided using nanoparticle compositions and spatial frequency heterodyne imaging for visualizing and detecting cells or a tissue such as a tumor, for identifying a potential therapeutic agent for treating a disease condition, and for preparing the nanoparticle compositions.

BACKGROUND

Hepatocellular carcinoma (HCC) is the most common form of liver cancer in adults, accounting for approximately three of every four cancers in the liver (El-Sarag et al. 1999, New England Journal of Medicine 340: 745-750). The American Cancer Society estimates that more than 24,000 new cases of primary liver cancer develop each year in the United States, of which approximately 19,000 result in death. HCC is common in developing countries, particularly in sub-Saharan Africa and Southeast Asia (Trevisani et al. 2008 Carcinogenesis 29: 1299-1305; and O'Brien 2004 Cancer Journal 10: 67-73).

More than 500,000 people are diagnosed with HCC each year worldwide (Trevisani et al. 2008 Carcinogenesis 29: 1299-1305; and Bruix et al. 2006 Oncogene 25: 3848-3856). HCC is difficult to diagnose in its earliest stages because there are currently no screening tests available, and HCC generally becomes symptomatic when the tumor is approximately 4.5 centimeters to eight centimeters in diameter (Trevisani et al. 2008 Carcinogenesis 29: 1299-1305; and Colombo 1992 Hepatol 15: 225-236).

Detection by ultrasound and imaging by computed tomography (CT) scans or magnetic resonance imaging (MRI) lack ability to definitively and reproducibly diagnose early stage cancers, particularly small HCC tumors (Bruix et al. 2006 Oncogene 25: 3848-3856; Hain et al. 2004 Cancer Journal 10: 121-127; Okuda 2000 J. Hepatol 32: 225-237; and Sheu et al. 1985 S. Cancer 56: 660-666). Misdiagnosis of HCC yielding false positive or false negative results is common from these imaging techniques, and the American Cancer Society estimates that HCC patients have a five-year survival rate of just 10%.

New techniques for imaging and early diagnosis of HCC and other cancers are needed to improve prognosis of cancers such as HCC.

SUMMARY

An aspect of the invention provides a method of imaging cells or a tissue, the method including: contacting a sample of the cells or the tissue with a nanoparticle composition containing at least one selected from the group of: a nanoparticle, a polymer layer coating the nanoparticle, and a binding agent that specifically binds a molecular species; irradiating the sample with an X-ray beam; and, detecting by X-ray scatter imaging the nanoparticle in the cells or the tissue. In various embodiments, the polymer layer is composed of at least one of: a polyethylene glycol, a polyelectrolyte, an anionic polymer, and a cationic polymer. The polyelectrolyte in various embodiments includes a protein, organic acid, or a polysaccharide; for example the polyelectrolyte is a poly(acrylic acid) or a poly(allylamine hydrochloride).

The method in various embodiments further includes prior to contacting, constructing the nanoparticle with at least one of: a metal, a metal oxide, an inorganic material, an alloy, and an organic material. In a related embodiment, the method further includes prior to contacting, constructing the nanoparticle with a MRI agent, a positive contrast agent, or a negative contrast agent. For example, the MRI agent includes an oil, a metal (e.g., iron and magnesium) sulfate, a metal chloride, or a metal ammonium citrate.

The method in various embodiments further includes prior to contacting, constructing the nanoparticle with at least one of: silver, copper, gold, cadmium, zinc, nickel, palladium, platinum, rhodium, platinum, manganese, gadolinium, dysprosium, tantalum, titanium, and iron. For example, the nanoparticle includes gadolinium-diethylene triamine pentaacetic acid (DTPA).

In various embodiments, the nanoparticles comprise a metallic core or a metallic shell. In various embodiments, the shell electron density is greater than the core electron density. Alternatively, in certain embodiments the core electron density is greater than the shell electron density. In various embodiments, the nanoparticles are non-toxic or biocompatible.

In an embodiment of the method, constructing the nanoparticle involves producing the nanoparticle to have an average diameter of at least about five nanometers (nm). In various embodiments of the method, the nanoparticle has a diameter of at least about: two nm, five nm, ten nm, 20 nm, 30 nm, 40 nm, 50 nm, 60 nm, 70 nm, 80 nm, 90 nm, or at least about 100 nm. In an alternative embodiment of the method, the nanoparticle is less than about 100 nm in diameter. In an embodiment of the method, constructing the nanoparticle includes engineering a plurality of nanoparticles having an average diameter greater than about five nm and less than about 100 nm.

In various embodiments of the method, irradiating the sample includes locating or inserting an absorption grid adjacent to the sample between an X-ray source and a detector. In certain embodiments, the method involves placing the absorption grid millimeters, centimeters or meters in the vicinity of or adjacent to the sample. The method in certain embodiments involves placing the absorption grid between an x-ray source and the sample, or alternatively in between the sample and the detector.

Detecting the presence of the nanoparticles in various embodiments of the method involves spatial frequency heterodyne imaging, spatial harmonic imaging. The terms, "spatial frequency heterodyne imaging" and "spatial harmonic imaging" are used interchangeably herein. In various embodiments, the spatial frequency heterodyne imaging involves performing a Fourier transformation of x-ray scatter images obtained by the detector. For example, the detector includes a light sensor such as a camera or a charge-coupled device.

In various embodiments of the method, the binding agent attached or conjugated to the nanoparticle includes at least one molecule selected from the group of: a drug, a protein, a carbohydrate, and a nucleotide sequence. In various embodiments of the method, the protein is an antibody selected from the group of: a monoclonal antibody; a polyclonal antibody; a single-chain antibody (scFv); a recombinant heavy-chain-only antibody (VH); an Fv; a Fab; a Fab'; and a F(ab')$_2$. In related embodiments of the method, the antibody (e.g., a monoclonal antibody and a polyclonal antibody) specifically binds a tumor antigen selected from the group of: aspartyl (asparaginyl)-β-hydroxylase, alpha-fetoprotein, carcinoembryonic antigen (CA), CA-125, mucin 1, epithelial tumor antigen, tyrosinase, melanoma-associated antigen, tumor protein 53, human chorionic gonadotropin, vimentin, CD34, desmin, prostate specific antigen, and glial fibrillary acidic protein. For example, the monoclonal antibody used in the method includes all or a portion of FB50 antibody (Wands et al. U.S. Pat. No. 6,797,696 issued Sep. 28, 2004), or SF25 antibody (Wands et al. U.S. Pat. No. 5,212,085 issued May 18, 1993).

In a related embodiment, the binding agent binds to or targets genetic material (e.g., a nucleotide sequence) in the cell. In various embodiments, the genetic material includes a DNA or an RNA, such that the RNA is selected from: mRNA, tRNA, rRNA, siRNA, RNAi, miRNA, and dsRNA, or a portion thereof. In certain embodiments, the binding agent binds to a cell surface receptor or to an intracellular receptor.

In various embodiments, the method images the tissue that contains a plurality of cells selected from at least one of the group of: cancerous, non-cancerous, epithelial, hematopoietic, stem, spleen, kidney, pancreas, prostate, liver, neuron, breast, glial, muscle, sperm, heart, lung, ocular, brain, bone marrow, fetal, blood, leukocyte, and lymphocyte. For example, the tissue is a sample obtained from a subject for example the tissue is a portion of an organ (e.g., a liver, heart, brain, and stomach).

In certain embodiments of the method, the binding agent attached or conjugated to the nanoparticle binds to an antigen, or a nucleotide sequence that encodes the antigen. For example, the antigen is a cancer antigen or a tumor antigen. In various embodiments, the method further includes diagnosing or prognosing a disease condition in the subject.

In various embodiments, the method further includes detecting or imaging a tumor in the cells or the tissue, wherein the tumor is selected from the group consisting of: melanoma; colon carcinoma; pancreatic; lymphoma; glioma; lung; esophagus; mammary; prostate; head; neck; ovarian; stomach; kidney; liver; and hepatocellular carcinoma.

In various embodiments, the method further includes administering a therapeutic agent to the cells, the tissue, or to the subject. In various embodiments, the therapeutic agent is at least one of: an antibiotic, an anti-viral, an anti-cancer, an anti-tumor, an anti-proliferative, and an anti-inflammatory.

An aspect of the invention provides a method of identifying in a model system a potential therapeutic agent for treating or preventing a disease condition, the method including: contacting a first sample and a second sample of cells or tissue having the disease condition with a composition containing: a nanoparticle and at least one of a polymer layer coating the nanoparticle and a binding agent that specifically binds the disease agent; contacting the second sample with the potential therapeutic agent; and, measuring a presence or an amount of a marker in the first sample and the second sample, such that the marker is characteristic of the disease condition, such that a greater amount of the marker in the first sample compared to that in the second sample is a measure of treatment and protection by the potential therapeutic agent, thereby identifying the potential therapeutic agent for treating or preventing the disease condition. In various embodiments of the method, the composition includes a plurality of nanoparticles.

Detecting the presence of the marker in the first sample and the second sample includes in various embodiments of the method measuring or detecting the nanoparticle using X-ray scatter imaging or spatial frequency heterodyne imaging.

In various embodiments, prior to contacting, the method further includes constructing the nanoparticle or a plurality of nanoparticles comprising at least one material selected from the group of: a metal, a metal oxide, a MRI agent, and a combination thereof.

In various embodiments, constructing the nanoparticles involves a layer-by-layer coating of one or more polymers on the nanoparticles. For example, at least one of the polymers is selected from: a polyethylene glycol, a polyelectrolyte, an anionic polymer, and a cationic polymer.

In various embodiments of the method, constructing the nanoparticle includes forming a shell or core of the nanoparticle with at least one from the group of: silver, copper, gold, cadmium, zinc, nickel, palladium, platinum, rhodium, platinum, manganese, gadolinium, dysprosium, tantalum, titanium, and iron. In a related embodiment of the method, constructing the nanoparticle involves vapor-phase synthesis.

In certain embodiments of the method, the binding agent includes at least one molecule selected from the group of: a drug, a protein, a carbohydrate, and a nucleotide sequence.

In various embodiments of the method, the disease condition is associated with or produced by at least one from the group of: a virus, a tumor, a cancer, a fungus, a bacterium, a parasite, a pathogenic molecule, and a protein. For example, the cancer is a carcinoma such as a hepatoma or a melanoma.

Prior to contacting, the method in various embodiments further includes constructing the nanoparticle by attaching or conjugating the binding agent to an external surface of the nanoparticle, such that the binding agent comprises at least one selected from the group of: a drug, a protein, a carbohydrate, and a nucleotide sequence. The protein in various embodiments is an antibody selected from the group of: a monoclonal antibody; a polyclonal antibody; a single-chain antibody (scFv); a recombinant heavy-chain-only antibody (VHH); an Fv; a Fab; a Fab; and a F(ab')$_2$.

In various embodiments of the method, measuring further includes observing a localization of the marker or the nanoparticle in the cells or the tissue of the first sample and the second sample. For example, the nanoparticle (or plurality of nanoparticles) is located in the nucleus or is located in cytoplasm of a cell in the first sample and the second sample.

The method in various embodiments further includes spatial frequency heterodyne imaging the nanoparticles in the cells or the tissue using an absorption grid and a detector.

An aspect of the invention provides a kit for imaging cells or a tissue in a subject, the kit including: a composition containing a nanoparticle including at least one selected from the group of: a polymer layer and a binding agent, such that the composition binds to and/or is phagocytosed by the cells or the tissue; instructions for use, such that the instructions describe: contacting the cells or the tissue with the composition, and imaging the cells and the tissue and detecting X-ray scattering of the composition with a device; and a container.

The nanoparticles in various embodiments of the kit include at least one material selected from the group of: a metal, a metal oxide, an inorganic material, an organic material, a MRI agent, and a combination thereof.

An aspect of the invention provides a composition for imaging cells or a tissue, the composition including: a metal nanoparticle having attached to an external surface of the nanoparticle a polymer layer, and FB50 monoclonal antibody that specifically binds an antigen of hepatocellular carcinoma, such that the polymer layer comprises at least one of: a polyethylene glycol, a polyelectrolyte, an anionic polymer, and a cationic polymer.

BRIEF DESCRIPTION OF THE DRAWINGS

FIG. 1 Gold (Au) nanoparticles were contacted with PAA to produce PAA-encapsulated nanoparticles (AU-PAA) having carboxylic acid functional groups (—COOH) and de-protonated carboxylic acid functional groups (—COO$^-$) extending from the nanoparticles. The PAA-encapsulated nanoparticles were contacted with PAH to form PAA-PAH encapsulated nanoparticles (Au-PAA-PAH). The PAH layer lies outside the PAA layer of PAA-PAH encapsulated nanoparticle resulting in amine functional groups (—NH$_2$) and protonated amino functional groups (—NH$_3^+$) extending from the nanoparticle.

FIG. 3 bottom right) corresponds to the original X-ray absorption image without scatter and is used for normalization. The image from the central $0^{th}$-order peak is subtracted from the higher order images to remove all absorption features. The area around the $1^{st}$-order peak (F$^{-1}$; S1: $1^{st}$ order left; FIG. 3 center bottom) corresponds to scattering in the x-direction, and therefore gives a processed left $1^{st}$-order scatter image upon Fourier back-transformation and normalization. Similarly, the area around the $1^{st}$-order peak immediately above the $0^{th}$-order peak (FIG. 3 top right box) corresponds to scattering in the y-direction, and therefore gives a processed upper $1^{st}$-order scatter image upon Fourier back-transformation and normalization. Each X-ray image yields at least two processed images; one image results from X-radiation scattered horizontally (F$^{-1}$; S1: $1^{st}$ order left; FIG. 3 center bottom), and the other image results from X-radiation scattered vertically (FIG. 3 top right box). Both $1^{st}$ order images measure identical scatter signals because of the isotropic scattering of the spherical nanoparticles.

FIG. 4 panel A is a camera photograph of FOCUS cell pellets under cell culture medium. Pellets of cells contacted with ten nm PAA-PAH coated gold nanoparticles (FIG. 4 panel A left vial) and with 50 nm PAA-PAH coated gold nanoparticles (FIG. 4 panel A right vial) are visibly darker in appearance that control pellets of cells not contacted with the gold nanoparticles (FIG. 4 panel A center vial).

FIG. 4 panel B is an absorption image of the vials containing FOCUS cell pellets contacted with ten nm PAA-PAH coated gold particles (right image), contacted with 50 nm PAA-PAH coated gold particles (left image), or control pellets of cells not contacted with the gold nanoparticles (center image).

FIG. 4 panel C is an left 1st-order processed image of the vials containing FOCUS cell pellets contacted with ten nm PAA-PAH coated gold particles (right image), contacted with 50 nm PAA-PAH coated gold particles (left image), or control pellets of cells not contacted with the gold nanoparticles (center image).

FIG. 4 panel D is an upper 1st-order processed image of the vials containing FOCUS cell pellets contacted with ten nm PAA-PAH coated gold particles (right image), contacted with 50 nm PAA-PAH coated gold particles (left image), or control pellets of cells not contacted with the gold nanoparticles (center image).

FIG. 6 panel A is a line graph of the overall average diameter in nm of: PEG-coated 50 nm gold nanoparticles (AU-PEG; middle peak), PEG-coated FB50 antibody conjugated 50 nm gold nanoparticles (AU-PEG-FB50; right most peak); and control 50 nm nanoparticles that were neither coated with PEG nor conjugated with FB50 (AU; left most peak). Data show that the diameter of the FB50 antibody conjugated 50 nm gold nanoparticles (93.9±12.1 nm) was larger than PEG-coated 50 nm gold nanoparticles (81.8±12.1 nm) and control gold nanoparticles (71.3±10.0 nm).

FIG. 6 panel B is a bar graph showing average percent uptake (Average % yield) of FOCUS cell pellets (checkered; three left columns) and NIH/3T3 cell pellets (solid; two right columns) contacted with conjugated ten nm gold nanoparticles. The FOCUS cell pellets were contacted with one of: PEG-coated ten nm gold nanoparticles (FOCUS+AU-PEG; left most column); PEG-coated FB50 antibody-conjugated ten nm gold nanoparticles (FOCUS+AU-PEG-FB50; second column from left); or PEG-coated MUK antibody-conjugated 50 nm gold nanoparticles (AU-PEG-FB50; third from the left). The NIH/3T3 cell pellets were contacted with either: PEG-conjugated ten nm gold nanoparticles (FOCUS+AU-PEG; second column from the right); or PEG-coated FB50 antibody-conjugated ten nm gold nanoparticles (FOCUS+AU-PEG-FB50; right most column). Data show that at least thirty fold more of the PEG-coated FB50 antibody conjugated ten nm gold nanoparticles were transported into the FOCUS cell pellets than into the NIH/3T3 cell pellets.

FIG. 7 panel A is a set of photographs (left column) and X-ray scatter images (right column) of livers of subjects injected with either saline (top row) or with PEG-coated 50 nm gold nanoparticles (AU-PEG; bottom row). The sizes of the livers for the subjects injected with saline or with nanoparticles were comparable. Improved X-ray scatter image clarity and sensitivity were observed in livers of subjects injected with PEG-coated 50 nm gold nanoparticles (FIG. 7 panel A right column bottom row) compared to subjects injected with saline only (FIG. 7 panel A right column top row).

FIG. 7 panel B is a set of total absorption images (left) and a X-ray total scatter images (right) of excised livers from subjects injected with either saline (top image) or PEG-coated 50 nm gold nanoparticles (AU-PEG; bottom image). The X-ray scatter images (right) more clearly delineated the actual size of the livers for the subjects compared to the absorption images (left), and the nanoparticles enhanced the imaging of the livers compared to the saline.

DETAILED DESCRIPTION

Figure 1:
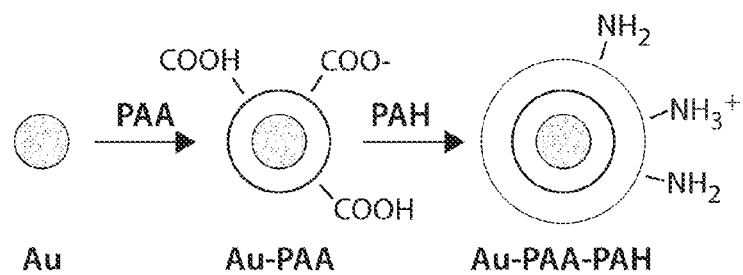
FIG. 1 is a drawing of methods for layer-by-layer polyelectrolyte coating of gold nanoparticles using an anionic poly(acrylic acid) (PAA), and a cationic poly(allylamine hydrochloride) (PAH).

Nanoparticles are structures/particles that have an approximate size of one nm to 100 nm and are used in applications, including addition to surfaces or fluids for catalytic reactions, self-cleaning and antibacterial products, glass dyeing, sunscreen lotions and manufacturing of optical components (e.g., optical fibers). See Rajala et al. U.S. Pat. No. 8,231,369 issued Jul. 31, 2012. Nanoparticles are composed of a variety of materials including metals, metal oxides, MRI agents, semiconductors, and polymers, and possess unique characteristics because of their small size.

Laboratory-scale and industrial-scale techniques are used to manufacture nanoparticles having for example a specific size distribution (mono-dispersivity), anti-agglomeration, and homogeneity (see Davis et al. U.S. Pat. No. 8,263,035 issued Sep. 11, 2012; Magdassi et al. U.S. Pat. No. 8,227,022 issued Jul. 24, 2012; and Fiannaca et al. U.S. patent application number US 2008/0050592 A1 published Feb. 28, 2008). Nanoparticles are produced for example by wet chemical processes and by vapor phase processes (see Murphy et al. U.S. Pat. No. 8,241,922 issued Aug. 14, 2012; and Brooks et al. U.S. Pat. No. 7,985,398 issued Jul. 26, 2011). Vapor phase processes (also known as aerosol reactor processes) use a number of different devices and techniques including: flame reactors, hot-wall reactors, plasma reactors, gas condensation methods, laser ablation and spray pyrolysis (see Jun et al. U.S. Pat. No. 7,988,761 issued Aug. 2, 2011; and Yang, Y. et al. 2006 Catalysis Communications 7:281-284) to synthesize nanoparticles of controlled size and composition.

Nanoparticles composed of metals are used as imaging agents that are imaged using a number of different techniques including MRI, ultrasonography, and X-ray computer tomography (see Grinstaff et al. U.S. Pat. No. 5,505,932 issued Apr. 9, 1996). Imaging of nanoparticles containing for example gadolinium, dysoprium, manganese, iron, and platinum involves specialized excitation and data manipulation of detected radiofrequency signals from non-zero spin nuclei which have a non-equilibrium nuclear spin state distribution. (Weiler et al. U.S. Pat. No. 6,370,415 issued Apr. 9, 2002; and Weiler et al. U.S. Pat. No. 6,595,211 issued Jul. 22, 2003). In conventional MRI the nuclei responsible for the detected signals are protons (e.g., protons of water), and the non-equilibrium spin state distribution is achieved by placing the subject in a strong magnetic field (to enhance the population difference between the proton spin states at equilibrium), and then exposing the subject to pulses of radiofrequency radiation at the proton Larmor frequency, which excites spin state transitions and creates a non-equilibrium spin state distribution (see Seri et al. U.S. Pat. No. 5,811,077 issued Sep. 22, 1998).

Nanoparticles such as gold nanoparticles are potential contrast agents for X-ray imaging because the nanoparticles are constructed to be non-toxic and to have a higher atomic number and X-ray absorption coefficient than typical iodine-based contrast agents (Hainfeld, J. F. et al. 2006 Br. J. Radiol. 79: 248-253; Kim, D. et al. 2007 J. Am. Chem. Soc. 129: 7661-7665; and Kojima, C. et al. 2010 Nanotechnology 21: 245104). Biodistribution for example of small gold nanoparticles injected intravenously is detected by X-ray imaging (Hainfeld, J. F. et al. 2006 Br. J. Radiol. 79: 248-253). Gold nanoparticles approximately 30 nm in diameter have been injected intravenously and used for in vivo computed tomography (CT) imaging of hepatoma in the liver (Kim, D. et al. 2007 J. Am. Chem. Soc. 129: 7661-7665). However, successful CT scan and MRI imaging of tissues required in vivo injection of large quantities of gold nanoparticles, or creating a high density of such particles at the image target for example, by linking the nanoparticles to targeted delivery vehicles.

Without being limited by any particular theory or mechanism of action, it is here envisioned that the spatial frequency heterodyne imaging/spatial harmonic imaging techniques described in Examples herein have the advantage of using a much reduced amount of nanoparticles (e.g., gold nanoparticles) to produce a visibly-enhanced contrast compared to typical absorption based X-ray imaging. Additionally, the imaging described herein using nanoparticles provides a nearly background-free image because scattered x-radiation is very well separated from transmitted radiation due to the different angles at which the scattered radiation reaches a detector.

X-rays employed for medical diagnostic imaging are electromagnetic radiation of approximately 0.01 nm to ten nm wavelength and high energy, approximately 100 electronvolts to 100 kiloelectronvolts (keV) and typically about two keV to 50 keV. A beam of X-rays directed to an atom is absorbed or deflected. The deflected X-rays define extent of scatter. Compton scattering describes an incident X-ray photon that is deflected from its original path by an electron. Scatter traditionally serves little purpose in imaging of tissues and patients, as scattering yields a diffuse signal that reduces contrast and clarity of the image (Feldmesser et al. U.S. Pat. No. 6,529,582 issued Mar. 4, 2003). Tissue images are generally prepared using only X-rays passed directly through the patient without colliding with atoms along the path. At a given point of the image plane or detector, the quantity of X-rays at that point indicates the degree of absorption of the primary beam in the patient on the line from the X-ray source to the X-ray receptor (e.g., the film). The scattered X-rays arrive at the X-ray film from various angles and places in the body not related to the path from the source to the receptor. Thus unwanted scattered X-rays cause the image to be distorted and cloudy. These distortions in the image from scattering result in reduced image contrast, and obscure the small variations in X-ray absorption that exist within the body of a subject, for which images should be obtained for an accurate diagnosis or prognosis.

Spatial frequency heterodyne imaging (also known as spatial harmonic imaging) was used in examples herein with an X-ray scatter reducing grid for absorbing rays scattered when radiation was transmitted through the subject, and to obtain a high quality image to reduce or eliminate scatter radiation. The grid was placed in the direction of propagation of an X-ray beam for example in parallel and in the shape of a flat plate or box. Radiation was transmitted through the grid and to a sample or a subject, such that the scattered radiation traveled obliquely and was absorbed and reduced by the radiation-absorbing portions. The primary radiation was transmitted (substantially linearly) through a vial containing the sample or through the subject. The primary radiation transmitted through the radiation-transmitting portions (e.g., wood, a metal, a plastic, and voids) of the grid and then the sample reached a detector that formed a radiation-transmitted image. The radiation-absorbing portions in certain embodiments are formed from an absorbing material or a dense shield material that attenuates x-radiation such as lead or the like. The radiation-transmitting portions and radiation-absorbing portions were in certain embodiments alternately or closely arranged, e.g., symmetrical positions. The radiation-transmitting portions have a high transmittance to avoid reducing transmission of the primary radiation to the sample and the detector (see Ogawa U.S. Pat. No. 6,707,884 issued Mar. 16, 2004; Stein, A. F. et al. 2010 Opt. Express 18: 13271-13278; Wen, H. et al. 2009 Radiology 251: 910-918; and Wen, H. et al. 2008 IEEE Trans Med Imaging 27: 997-1002, each of which is incorporated by reference herein in its entirety). Fourier transformation was is used to process the image produced by the detector (FIG. 1).

An imaging technique described herein involves in certain embodiments use of surface-modified gold nanoparticles and spatial frequency heterodyne imaging. The nanoparticles (containing at least one of a metal or a metal oxide) are modified in certain examples by attaching a binding agent and/or a polymer (e.g., a polyelectrolyte) layer. The nanoparticles were observed to be biocompatible and non-toxic and were taken up by cells.

Nanoparticles used in various embodiments of the invention were constructed using layer-by-layer coatings of polymers such as electrolytes. Layer-by-layer coating of polyelectrolytes is a versatile method for modifying the surface chemistry of nanoscale materials including gold nanoparticles and nanorods (Mayya, K. S. et al. 2003 Adv. Funct. Mater. 13: 183-188; Gittins, D. I. et al. 2001 J. Phys. Chem. B. 105: 6846-6852; Gole, A. et al. 2005 Chem. Mater. 17: 1325-1330; and Murphy, C. J. 2005 Chem. Mater. 17: 1325-1330). Layer-by-layer coatings of charged polyelectrolytes are useful to stabilize colloidal suspensions.

Deposition of polyelectrolyte coatings (e.g., poly(acrylic acid) and poly(allylamine hydrochloride) on surfaces of structures under specific pH conditions result in the ability of the coated surfaces to bind cells (Mendelsohn, J. D. et al. 2003 Biomacromolecules 4: 96-106). Poly(acrylic acid) and poly(allylamine hydrochloride) are weak polyelectrolytes with different degrees of ionization, and as a result each of these electrolytes has a strength of electrostatic interaction that is pH-dependent (Shiratori, S. S. et al. 2000 Macromolecules 33: 4213-4219). Poly(acrylic acid) stock solutions and poly(allylamine hydrochloride) stock solutions used in certain embodiments herein were adjusted to have a pH of 8.4 and 3.7, respectively, and under these conditions poly(acrylic acid) has a pKa of about 4.5 and poly(allylamine hydrochloride) has a pKa about 8.5. Stock solutions of poly(acrylic acid) and poly(allylamine hydrochloride) described herein were fully charged, i.e., anionically and cationically, respectively.

The de-protonated carboxylic acid groups of anionic poly(acrylic acid) (PAA) interacted strongly with protonated amine groups of cationic poly(allylamine hydrochloride) (PAH), such that the oppositely charged layers produced thin, flat coatings on the nanoparticle surface. Water is unable to penetrate the surface layer of the PAA-PAH coated nanoparticle because the PAA-PAH polyelectrolyte layers were so tightly cross-linked by the anionic and cationic (i.e., ionic) interactions. The electrolyte coated nanoparticles produced by this method therefore resulted in a very hydrophobic polymer barrier to a surrounding aqueous environment. The hydrophobicity of the electrolyte coating resulted in nanoparticle surfaces that were cytophilic (Lee, J. H. et al. 1995 Prog. Polym. Sci. 20: 1043-1079; Alexis, F. et al. 1998 Mol. Pharm. 5: 505-515; Brandenberger, C. et al. 2010 Small 6: 1669-1678). Furthermore, the thickness and specificity of the polyelectrolyte coating is controlled by varying and optimizing the number of layers deposited on the surface of the nanoparticles (Mayya, K. S. et al. 2003 Adv. Funct. Mater. 13: 183-188; and Gittins, D. I. et al. 2001J. Phys. Chem. B. 105: 6846-6852). Without being limited by any particular theory or mechanism of action, it is here envisioned that the polyelectrolyte-coated nanoparticles described herein were effective vehicles for cellular uptake by mechanisms such as phagocytosis and endocytosis.

Specificity of the nanoparticles was further enhanced by conjugating a variety of antibody binding agents to the polyelectrolyte coatings. Layer-by-layer coating and antibody binding agent conjugation of nanoparticle composition functionalized the nanoparticle compositions and increased the specific binding of the nanoparticles to different types of cells and tissues (Murphy, C. J. 2005 Chem. Mater. 17: 1325-1330). Phagocytosis of the polymer coated gold nanoparticles in living cells was measured in a model system using FOCUS cells, a human hepatocellular carcinoma (HCC) cell line (He, L. et al. 1984 In Vitro 20: 493-504). FOCUS cells are a model for the study of targeted imaging of cells because these cells express specific HCC antigens that are recognized and bound by binding agents such as monoclonal antibodies (Hurwitz, E. et al. 1990 Bioconjugate Chem. 1: 285-290; Takahashi, H. et al. 1989 Gastroenterology 96: 1317-1329; Mohr, L. et al. 2004 Gastroenterology 127: S225-S231; and Luu, M. et al. 2009 Hum. Pathol. 40: 639-644). A strong antibody-antigen interaction exists between FB50 antibody and aspartyl (asparaginyl)-β-hydroxylase, a protein over-expressed in liver cancer cells such as HCC (Luu, M. et al. 2009 Hum. Pathol. 40: 639-644).

Figure 5:
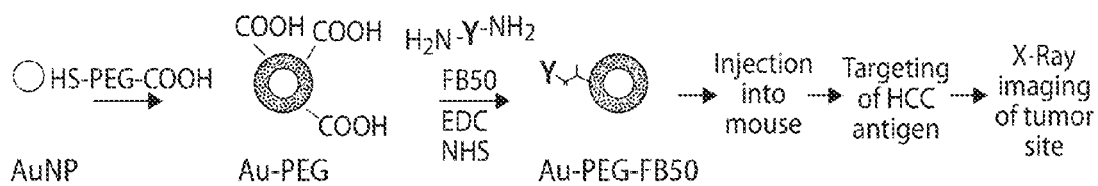
FIG. 5 is a drawing showing methods for producing a polyethylene glycol-coated FB50 antibody conjugated gold nanoparticles and injecting the nanoparticle into a subject having hepatocellular carcinoma (HCC). The FB50 antibody conjugated to the nanoparticle specifically targets an antigen of HCC and allows for imaging of a HCC tumor site using spatial harmonic imaging. The drawing shows contacting a gold nanoparticle (AuNP) with a bi-functional polyethylene glycol (PEG) having carboxylic acid functional groups (—COOH). The PEG undergoes facile attachment to the external surface of the nanoparticle (Au-PEG). The gold nanoparticle having attached PEG was bio-conjugated to FB50 antibody using carbodiimide-amine (EDC/NHS) linking chemistry. The polyethylene glycol coated, FB50 antibody conjugated gold nanoparticles (Au-PEG-FB50) were injected into a mouse having HCC, and the FB50 antibody component of the conjugated nanoparticle specifically bound to an antigen of HCC. Spatial harmonic imaging of the mouse resulted in imaging of the HCC tumor bound to the polyethylene glycol-coated FB50 antibody-conjugated gold nanoparticles.
Figure 6A:
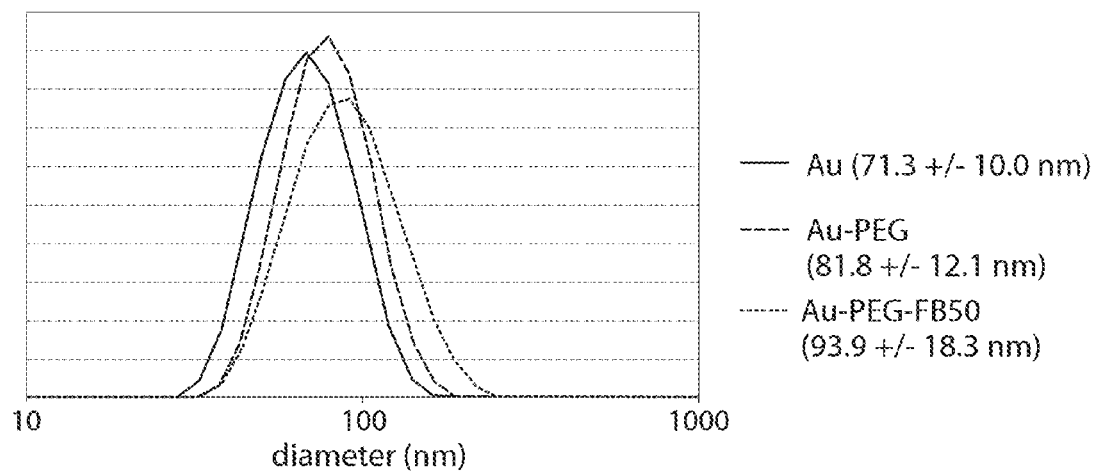
FIG. 6 panels A-B are graphs of calculation of overall diameter of coated or conjugated 50 nm gold nanoparticles, and uptake of the coated or conjugated ten nm gold nanoparticles by FOCUS cell pellets or by NIH/3T3 (a fibroblast cell line) cell pellets. FB50 antibody (specific for an antigen of HCC) or a control antibody specific for Murutucu tropical antibody (MUK) were conjugated to the nanoparticles. Data show that the PEG-coated, FB50 antibody conjugated nanoparticles produced by methods herein were effectively and specifically bound to and transported into the FOCUS cell pellets and not NIH/3T3 cell pellets.
Figure 6B:
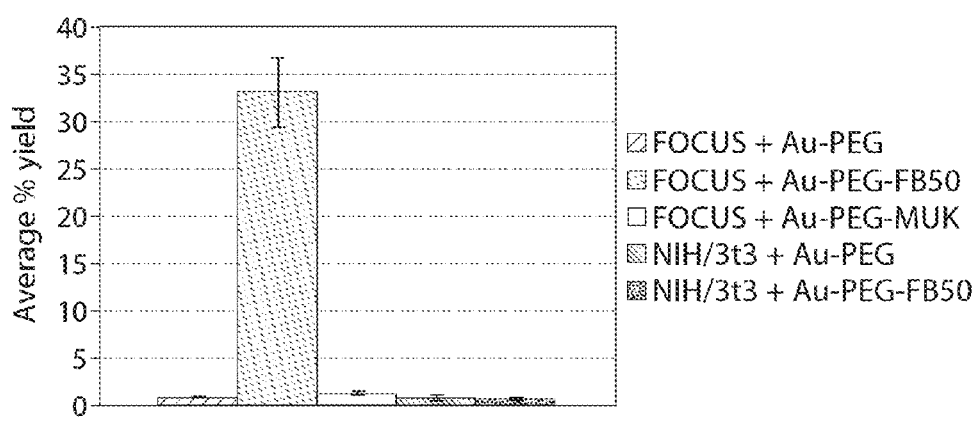
Figure 7A:
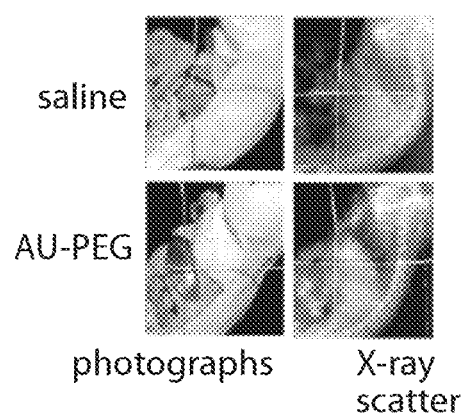
FIG. 7 panels A-B are a set of photographs, X-ray scatter images, and absorption images of mice injected in vivo either with PEG-coated 50 nm gold nanoparticles or with saline (negative control). Mice were injected in the tail vein twice in 24 hours and were sacrificed 48 hours after the first injection. Livers of subjects injected with the PEG-coated 50 nm gold nanoparticles showed a significant average signal enhancement (23.0±14.1%) compared livers from subjects injected with saline only.
Figure 7B:
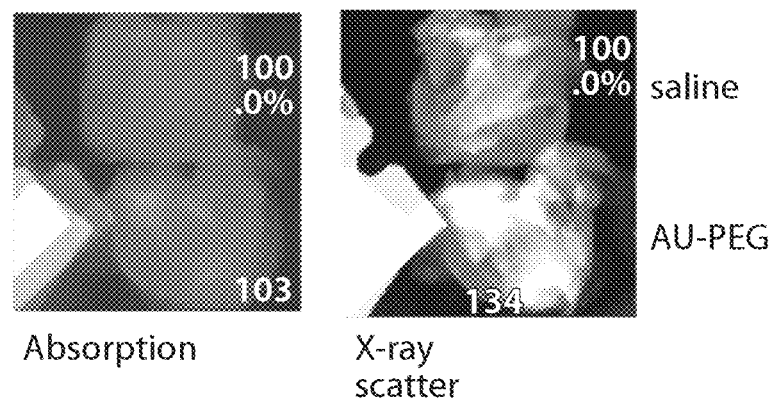

Examples herein used antibody-conjugated nanoparticles and spatial frequency heterodyne imaging to directly target and image tumors in an animal model (Mohr, L. et al. 2004 Gastroenterology 127: S225-S231; and Luu, M. et al. 2009 Hum. Pathol. 40: 639-644). The N-terminal (amino terminus) of FB50 antibody was conjugated to the outer surface of a PEG coated nanoparticle by 1-ethyl-3-3-dimethylaminopropyl]carbodiimide and amine (EDC/NHS) cross-linking chemistry (FIG. 5). In certain embodiments, the polymer (e.g., PEG, PAA, and PAH) coatings are mixed with and bound to the antibody binding agent prior to being contacted with the nanoparticle to produced a polymer-coated antibody-conjugated nanoparticle, which can be used for example to binding normal tissues or cancer tissues in vivo (FIGS. 6-7). In certain embodiments, the binding agent (e.g., protein) or plurality of binding agents is conjugated or attached to the nanoparticles at a carboxy-terminus or an amino-terminus.

Nanoparticles are coated with a polyethylene glycol (PEG) to prevent nonspecific protein adsorption, to reduce nonspecific cellular uptake, and to increase the circulation times of nanoparticles in the bloodstream (Alexis, F. et al. 1998 Mol. Pharm. 5: 505-515; Brandenberger, C. 2010 Small 6: 1669-1678; Hucknall, A. et al. 2009 Adv. Maert. 21: 2441-2446; and Lipka, J. et al. 2010 Biomaterials 31: 6574-6581). In certain embodiments, the PEG polymer layer was coated to gold nanoparticles using layer-by-layer coating techniques and then used to conjugate binding agents to the nanoparticles that target specific cancers in vivo (FIG. 5). The gold nanoparticles were then used to deliver gold to the HCC tumors, and the cells and the nanoparticles were imaged and diagnosed.

Cancer cells such as FOCUS cells were targeted in vivo by contacting the cells with nanoparticles conjugated with an FB50 antibody binding agent that binds to HCC antigens. The binding agent-conjugated nanoparticles contact the cells and/or or deliver therapeutic agents to the targeted cells, and avoid being taken up by healthy cells. Spatial frequency heterodyne imaging was performed on samples of pellets of FOCUS cells incubated with different amount of PAA-PAH coated gold nanoparticles (ten nm or 50 nm diameters). Control samples were incubated in absence of gold nanoparticles. Each set of pellets was imaged multiple times to exclude false signals due to possible non-uniformities of the sensitivity of the imaging system. A vial holder was designed and used to keep vials containing cell samples and nanoparticles in a position that could be reproduced. Apertures of the same size were drilled through a thin block of aluminum so that the vials, placed into these apertures, were positioned at exactly the same position and height.

Examples herein in certain embodiments used cell pellets each containing approximately $10^7$ FOCUS cells. The pellet size of FOCUS cells corresponded to the approximate size of a small tumor (several millimeters in diameter). The FOCUS cells were cultured and incubated with gold nanoparticles (ten nm and 50 nm diameter). Beams of X-rays were directed through an absorption grid and a vial containing the sample of cells, and the scatter X-ray radiation was detected using a charge-coupled camera (CCD). Fourier transformation of the X-ray scatter data produced by the spatial frequency heterodyne imaging yielded clear and sensitive images of the cells. Data herein show that spatial frequency heterodyne imaging of cells and tissues contacted with the nanoparticles was more sensitive than typical absorption-based imaging techniques, for example, tissues imaged with CT scans and MRI imaging.

Data show enhanced FOCUS cell phagocytosis of the gold nanoparticles having a bi-layer of PAA and the cationic PAH compared to phagocytosis of gold nanoparticles having no coating (FIG. 4). Presence of the polymer layers of polyelectrolytes on the nanoparticle surface resulted in nearly double amount of uptake of the nanoparticles by the FOCUS cells (see Table 1). The mass of gold taken up by each cell corresponds to several hundred 50 nm gold nanoparticles and tens of thousands of ten nm gold nanoparticles (Table 2).

TABLE 1

Cellular uptake of gold nanoparticles.

| | uncoated 10 nm nanoparticles | 10 nm PAA-PAH nanoparticles | 50 nm PAA-PAH nanoparticles |
|---|---|---|---|
| mass of gold taken up per cell (picograms) | 1.2 ± 0.5 | 2.8 ± 0.4 | 2.2 ± 0.3 |
| approximate number of nanoparticles per cell | 108,000 | 275,000 | 1730 |
| approximate volume fraction of nanoparticles in each cell | 0.00025% | 0.00063% | 0.00049% |

TABLE 2

Average signal enhancements of cells due to gold labeling incubation with PAA-PAH gold nanoparticles.

| | | replicate 1 | replicate 2 |
|---|---|---|---|
| mass of gold taken up per cell (pg) | | 0.45 ± 0.09 | 0.76 ± 0.11 |
| average number of | 10 nm | 44,600 | 75,200 |
| nanoparticles per cell | 50 nm | 356 | 602 |
| change in signal per | original image | 1.3 ± 4.4 | 1.1 ± 3.0 |
| pellet (%)[a] | processed image | 1.6 ± 0.3 | 4.4 ± 0.8 |
| signal enhancement | original image | 2.9 ± 9.8 | 1.4 ± 3.9 |
| per 1 pg of gold taken | processed image | 3.6 ± 0.7 | 5.7 ± 1.1 |
| up per cell (%) | | | |
| approximate potential signal enhancement for a pellet of $10^7$ cells (%) | | 11 ± 2 | 17 ± 3 |

[a]All enhancements are reported in logarithm scale.

A set of representative X-ray scatter imaging photographs of the pellets under cell culture medium shows gold labeling by the nanoparticles (see FIG. 4). Processed X-ray scatter images using spatial frequency heterodyne imaging showed significant image enhancement due to gold labeling by the polymer modified nanoparticles that was almost five-fold greater than enhancements identified in the absorption images (Table 2). Further, examples herein using polymer coated antibody-conjugated gold nanoparticle compositions produced data showing increased cellular uptake of gold nanoparticles into cells and tissues compared to results for cells contacted with only polymer coated gold nanoparticles (FIG. 6). For example, data herein showed that less than 0.001% of each cell volume is occupied by polymer coated gold nanoparticles, allowing for significantly increased amounts of gold nanoparticles to be further introduced into each cell, thereby increasing scatter signal and, ultimately, enhancing visibility in scatter images. The sensitivity and potential specificity of the nanoparticle-based imaging techniques described herein show that these are effective methods, compositions and kits for early detection and diagnosis of cancers such as HCC.

Examples herein show that cell pellet samples of FOCUS cells phagocytosed gold nanoparticles of different sizes, and that the gold nanoparticle-containing cell pellets of FOCUS cells were distinguishable from cell pellets of FOCUS devoid of gold nanoparticles using spatial frequency heterodyne imaging. Spatial frequency heterodyne images of FOCUS cell pellets labeled with gold nanoparticles showed that greater than 85% of the images indicate a signal enhancement compared to X-ray scatter images of FOCUS pellets containing no gold. Data herein showed that each FOCUS cell phagocytosed approximately three picograms of gold nanoparticles per cell (Table 1), and that X-ray scatter imaging enhances visibility by up to 5.7% for every picogram of gold in the cells (Table 2). Without being limited by any particular theory or mechanism of action, it is here envisioned that that spatial frequency heterodyne imaging enhanced visibility of gold nanoparticle-labeled cells by more than 17% on a logarithmic scale.

Examples herein obtained images of cell pellets that were several millimeters in diameter, which corresponds to the approximate size of a small tumor. Spatial frequency heterodyne imaging of nanoparticles was used in Examples to detect tumor-sized cell samples that are significantly below the detection limits of current imaging techniques for HCC and many other cancers. Currently cancers such as HCC go undiagnosed until the tumors are several centimeters in size, viz., the cancers are detected only upon reaching a size an order of magnitude greater than the sizes detected using the methods described herein for X-ray scatter imaging of nanoparticles. Thus, methods, compositions, and kits described herein were effective for imaging and for differentiating cancerous tissues and normal tissues.

Spatial frequency heterodyne imaging was performed on cell pellet samples that were placed under water in an in vivo model, because water and tissues (e.g., liver tissues) share a similar radiological density. Data showed that in vitro X-ray scatter imaging of the submerged cells and nanoparticles was effective in visualizing the cells. Without being limited by any particular theory or mechanism of action, it is here envisioned that spatial frequency heterodyne imaging of nanoparticles containing a metal as described herein would detect small in situ tumors (less than a few millimeters in size) in liver and in other internal organs and tissues.

Metal nanomaterials (containing for example gold) have been used for cancer therapy applications (e.g., introduction of bioactive agents) as well as imaging applications (see Sung et al. U.S. Pat. No. 7,985,426 issued Jul. 26, 2011). For example, gold nanoshells have been developed for use in photothermal cancer therapy (Hirsch, L. R. et al. 2003 Proc. Natl. Acad. Sci. U.S.A. 100: 13549-13544; Choi, M. et al. 2007 S, Nano Lett. 7: 3759-3765; Lal, S.; Clare, S. E. et al. 2008 Acc. Chem. Res. 41: 1842-1851). These nanoshells composed of metals and metal oxides have highly tunable plasmon resonances, allowing strong absorption of light even under the circumstances of the frequency of the incoming light matching plasmon oscillation frequencies of the nanoshells. The nanoshells convert energy absorbed from directed light into heat, killing cells containing the nanoshells and leaving unharmed the surrounding unlabeled cells and tissues. Clinical trials of therapies using nanoshells and nanostructures are being investigated (Clare, S. E. et al. 2008 Acc. Chem. Res. 41: 1842-1851).

Gold nanoparticles have also been used to provide dose enhancement in cancer radioablation therapy. Small gold nanoparticles have for example been injected intravenously such that the nanoparticles accumulated in tumors and improved X-ray therapy at the tumor site (Hainfeld, J. F. 2004 Physics in Medicine and Biology 49: N309-N315). As both of the therapeutic applications discussed above use electron-dense nanomaterials, it is envisioned herein that the X-ray scatter imaging methods and compositions described herein would be effective in combination with these and similar applications for the dual imaging and therapy of cells and tissues.

An aspect of the invention provides a composition for enhanced imaging and/or diagnosing a cells or a tissue for example a tumor, the composition including a nanoparticle having at least one polymer layer coating the nanoparticle, such that the nanoparticle binds to and/or is phagocytosed by the cells or the tissue to enhance visibility of the tumor by X-ray scatter imaging.

In an embodiment of the composition, the nanoparticle includes a metal, for example the metal is at least one of: silver, copper, gold, mercury, cadmium, zinc, nickel, palladium, platinum, rhodium, mercury. In an embodiment of the composition, the metal is a transition metal for example titanium or iron.

In an embodiment of the composition, the nanoparticle includes a shell of a material for example a metal or a carbon, surrounding a core of a material with an electron density lower than that of the shell. For example, a carbon core or a silica core is surrounded by a layer of gold or another suitable metal, metal oxide, MRI agent, inorganic material, or organic material.

In an embodiment of the composition, the nanoparticle is at least about five nm in diameter. In various embodiments of the composition, the nanoparticle has a diameter of at least about: two nm, five nm, ten nm, 20 nm, 30 nm, 40 nm, 50 nm, 60 nm, 70 nm, 80 nm, 90 nm, and 100 nm. In an embodiment, the nanoparticle includes a plurality of nanoparticles having an average diameter greater than about five nm.

In an embodiment of the composition, the nanoparticle is less than about 100 nm in diameter. In various embodiments of the composition, the nanoparticle includes a diameter less than about: 100 nm, 90 nm, 80 nm, 75 nm, 65 nm, 60 nm, 50 nm, 45 nm, 40 nm, 30 nm, 25 nm, 20 nm, 15 nm, and ten nm. In an embodiment, the nanoparticle includes a plurality of nanoparticles having an average diameter less than about 100 nm.

In an embodiment of the composition, the polymer layer includes at least one of: an anionic polyelectrolyte, a cationic polyelectrolyte, and a polyethylene glycol. In an embodiment of the composition, the polyethylene glycol polymer is about 10,000 average molecular weight in size. In other embodiments, the polyethylene glycol polymer includes an average molecule weight in size of at least one of: about 1,000; about 2,000; about 4,000; about 6,000; about 8,000; about 12,000; about 15,000; about 20,000; and about 30,000.

In an embodiment of the composition, the polymer layer includes an anionic polyelectrolyte. In various embodiments of the composition, the anionic polyelectrolyte is at least one selected from: a poly(acrylic acid), a 4-Styrenesulfonic acid, poly(2-acrylamido-2-methyl-1-propanesulfonic acid), a poly (2-acrylamido-2-methyl-1-propanesulfonic acid, a poly(4-styrenesulfonic acid), a poly(4-styrenesulfonic acid-co-maleic acid), a polyanetholesulfonic acid, a poly(vinylsulfonic acid), and a salt thereof. In various embodiments of the composition, the polymer layer is a bio-compatible layer or a non-toxic-layer.

In an embodiment of the composition, the polymer layer includes a cationic polyelectrolyte. In various embodiments of the composition, the cationic polyelectrolyte is at least one selected from: a diallyldimethylammonium, a poly(acrylamide-co-diallyldimethylammonium chloride), a poly(allylamine hydrochloride, a poly(diallyldimethylammonium chloride), and a salt thereof.

In an embodiment of the composition, the anionic polyelectrolyte and/or the cationic polyelectrolyte include an anionic poly(acrylic acid) and an cationic poly(allylamine hydrochloride), respectively.

The composition further includes for example at least one binding agent that selectively binds the nanoparticle to the tissue, for example, the binding agent includes at least one selected from the group of: a drug, a protein such as an antibody or a binding protein, a carbohydrate such as a sugar, and a nucleotide sequence. For example, the antibody is a polyclonal antibody, a monoclonal antibody, or a portion thereof for example a Fv; a Fab; a Fab'; or a F(ab')$_2$. In an embodiment of the composition, the antibody includes a fusion protein or a chimeric protein.

The tumor in various embodiments of the composition is located or associated with a site or cancer selected from the group of: melanoma; sarcoma; carcinoma (e.g., colon and hepatocellular); pancreatic; lymphoma; glioma; lung; esophagus; mammary; prostate; head; neck; ovarian; kidney; and liver.

An aspect of the invention provides a composition including: a gold nanoparticle; a polymer layer coating the nanoparticle comprising for example a polyethylene glycol or a polyelectrolyte such as an anionic poly(acrylic acid), and a cationic poly(allylamine hydrochloride); and, a monoclonal antibody or portion thereof that specifically binds a tumor antigen and is bound to the polymer layer.

In an embodiment of the composition, the nanoparticle is at least about five nm in diameter. In an embodiment of the composition, the nanoparticle is less than about 100 nm in diameter. For example, the nanoparticle is about ten nm or about 50 nm in diameter.

In an embodiment of the composition, the monoclonal antibody is FB50 and the tumor antigen is aspartyl (asparaginyl)-β-hydroxylase. In an embodiment of the composition, the tumor antigen is associated with hepatocellular carcinoma.

An aspect of the invention provides a method of diagnosing a presence of a tumor in a subject including: contacting a tissue with a composition having: a gold nanoparticle; a polymer layer coating the nanoparticle, such that the polymer layer comprises for example a polyethylene glycol or a polyelectrolyte such as an anionic poly(acrylic acid) or a cationic poly(allylamine hydrochloride); and, a binding agent that specifically binds a tumor antigen, such that the binding agent is bound to the polymer layer; and, detecting the presence or absence of the tumor attached to the nanoparticle using an imaging device, such that detecting comprises identifying presence or accumulation the nanoparticles in the tissue by X-ray scatter imaging to detect the tumor. In an embodiment of the method, the tissue is in situ or in vivo. Alternatively, the tissue is in vitro, for example the method in an embodiment includes, prior to contacting the tissue with the composition, collecting or obtaining the tissue from the subject.

In various embodiments of the method, the imaging device includes a X-ray device or a MRI device. In various embodiments of the method, detecting using the X-device involves generating X-rays using an X-ray tube or laser or accelerator generated X-rays.

In an embodiment of the method, detecting the presence of the tumor includes spatial frequency heterodyne imaging or spatial harmonic imaging, for example the spatial harmonic imaging involves irradiating with an X-ray source and detecting with an absorption grid, and/or a detector. In an embodiment of the method, detecting the presence of the tumor involves identifying in situ the presence of the tumor. Alternatively, detecting involves identifying in vitro the presence of the tumor.

In various embodiments of the method, the nanoparticle includes at least one of: silver, copper, gold, mercury, cadmium, zinc, nickel, palladium, platinum, rhodium, mercury, and a combination thereof.

In various embodiments of the method, the anionic poly (acrylic acid) is directly contacting the nanoparticle, and the cationic poly(allylamine hydrochloride) and the polyethylene glycol coat the anionic poly(acrylic acid).

The method in an embodiment further includes prior to contacting the tissue, preparing the nanoparticle by coating the nanoparticle with the polymer layer and attaching the binding agent.

In various embodiments of the method, the tissue includes a plurality of cells selected from the group of: epithelial cells, hematopoietic cells, stem cells, spleen cells, kidney cells, pancreas cells, liver cells, neuron cells, glial cells, smooth or striated muscle cells, sperm cells, heart cells, lung cells, ocular cells, bone marrow cells, fetal cells, peripheral blood mononuclear cells, leukocyte cells, lymphocyte cells, and living postmitotic cells.

In an embodiment of the method, the binding agent includes at least one selected from the group of: a drug, a protein, a carbohydrate, and a nucleotide sequence. In an embodiment of the method, the binding agent includes a polyclonal antibody or a portion thereof. In an embodiment of the method, the binding agent includes a monoclonal antibody or a portion thereof. In an embodiment of the method, the antibody is specific for the tumor antigen selected from the group of: aspartyl (asparaginyl)-β-hydroxylase, alphafetoprotein, carcinoembryonic antigen (CA), CA-125, mucin 1, epithelial tumor antigen, tyrosinase, melanoma-associated antigen, tumor protein 53, human chorionic gonadotropin, vimentin, CD34, desmin, and glial fibrillary acidic protein. For example, the binding agent is monoclonal antibody FB50 or SF25. In various embodiments of the method, the antibody is an immunoglobulin selected from the group consisting of: IgA, IgD, IgE, and IgG. In an embodiment of the method, the antibody is from at least one origin selected from: human, murine, ovine, bovine, feline, canine, hircine, and equine.

In various embodiments of the method, the tumor is selected from the group of: melanoma; colon carcinoma; pancreatic; lymphoma; glioma; lung; esophagus; mammary; prostate; head and neck; ovarian; kidney; liver, and hepatocellular carcinoma.

The method in an embodiment further includes therapeutically treating the tumor, for example to surgically excising the tumor or to reduce size of the tumor. In various embodiments, the method further includes administering a therapeutic agent to the tumor or to the subject. In various embodiments, the therapeutic agent is at least one of: an anti-cancer, anti-tumor, an anti-proliferative, and an anti-inflammatory.

An aspect of the invention provides a method of manufacturing a composition for imaging and/or diagnosing a tumor involving: coating a nanoparticle with a polymer layer, such that the polymer layer coats the nanoparticle and includes for example a polyethylene glycol and/or a polyelectrolyte such as an anionic poly(acrylic acid) or a cationic poly(allylamine hydrochloride), to obtain a resulting polymer-coated nanoparticle; and contacting the resulting polymer-coated nanoparticle with at least one binding agent that selectively attaches to the polymer layer and binds the tumor, thereby producing the composition for imaging and/or diagnosing the tumor. In an embodiment, the polymer layer includes both the polyethylene glycol and the polyelectrolyte layer.

In an embodiment of the method, the binding agent that binds the tumor includes at least one selected from the group of: a drug, a protein, a carbohydrate, and a nucleotide sequence.

In an embodiment of the method, the binding agent includes a monoclonal antibody that specifically targets the tumor or a surface protein or peptide located on the tumor. For example, the binding agent is monoclonal antibody FB50 or monoclonal antibody SF25.

In an embodiment of the method, the antibody includes a polyclonal antibody that specifically targets the tumor or a surface protein or peptide located on the tumor.

In various embodiments of the method, the binding agent binds a tumor antigen that is at least one selected from the group of: aspartyl (asparaginyl)-β-hydroxylase, alphafetoprotein, carcinoembryonic antigen (CA), CA-125, mucin 1, epithelial tumor antigen, tyrosinase, melanoma-associated antigen, tumor protein 53, vimentin, CD34, desmin, and glial fibrillary acidic protein.

In various embodiments of the method, the tumor is selected from the group of melanoma; colon carcinoma; pancreatic; lymphoma; leukemia; glioma; lung; esophagus; mammary; prostate; head and neck; ovarian; kidney; liver, and hepatocellular carcinoma.

The method in an embodiment includes prior to contacting the nanoparticle with at least one polymer layer, constructing the nanoparticle to have a diameter greater than about five nm in diameter, or to have a diameter less than about 100 nm in diameter.

An aspect of the invention provides a kit for diagnosing presence of a tumor in a subject with a composition, the kit including: a nanoparticle; a polymer layer coating the nanoparticle, having: a polyethylene glycol or a polyelectrolyte such as an anionic poly(acrylic acid) and/or a cationic poly (allylamine hydrochloride); and, a binding agent that specifically binds a tumor antigen, wherein the antibody is bound to the polymer layer; the kit further including instructions for use and a container.

In an embodiment of the kit, the nanoparticle comprises a metal, for example a transition metal. In various embodiments of the kit, the metal includes at least one of: silver, copper, gold, mercury, cadmium, zinc, nickel, palladium, platinum, rhodium, mercury, and a combination thereof.

In an embodiment of the kit, the anionic poly(acrylic acid) contacts the nanoparticle, and the cationic poly(allylamine hydrochloride) contacts the anionic poly acrylic acid.

In an embodiment of the kit, the binding agent includes at least one selected from the group of: a drug, a protein, a carbohydrate, and a nucleotide sequence. In an embodiment of the kit, the binding agent that selectively attaches the composition to the tumor is an antibody or a portion thereof, for example the antibody includes a monoclonal antibody or a portion thereof. In an embodiment of the invention, the antibody includes a polyclonal antibody or a portion thereof.

In an embodiment of the kit, the binding agent is monoclonal antibody FB50 or monoclonal antibody SF25, or a portion thereof.

In an embodiment of the kit, the tumor is selected from the group of: melanoma; colon carcinoma; pancreatic; lymphoma; glioma; lung; esophagus; mammary; prostate; head and neck; ovarian; kidney; liver, and hepatocellular carcinoma. In certain embodiments, the kit includes any pharmaceutical composition described herein.

In various embodiment of the kit, the tumor antigen is at least one selected from the group of: aspartyl (asparaginyl)-β-hydroxylase, alphafetoprotein, carcinoembryonic antigen (CA), CA-125, mucin 1, epithelial tumor antigen, tyrosinase, melanoma-associated antigen, tumor protein 53, vimentin, CD34, desmin, and glial fibrillary acidic protein.

An aspect of the invention herein provides a method of identifying in a model system a potential therapeutic agent for treating or preventing a tumor, the method including: contacting a first sample of cells or tissue having a tumor with a composition including: a gold nanoparticle; a polymer layer coating the nanoparticle comprising for example a polyethylene glycol or a polyelectrolyte, for example the polyelectrolyte includes an anionic poly(acrylic acid) or a cationic poly(allylamine hydrochloride); and, a monoclonal antibody that specifically binds a tumor and is bound to the polymer layer, contacting a second sample of the cells or tissue having the tumor with the composition and a potential therapeutic agent; and measuring in the first sample and the second sample, an amount of the marker, such that the marker is characteristic of the tumor, such that the amount of the marker in the second sample compared to that in the first sample is a measure of treatment and protection by the potential therapeutic agent, such that a decreased amount of the marker in the second sample compared to the first sample is an indication that the potential therapeutic agent is therapeutic, thereby identifying the potential therapeutic agent for treating or preventing the tumor. In an embodiment of the method, measuring further comprises detecting the presence of the tumor in first sample and the second sample using X-ray scatter imaging, for example spatial harmonic imaging.

An aspect of the invention provides a composition for imaging and/or diagnosing a tumor including: nanoparticles having at least one binding agent that binds to and/or is suitable for phagocytosis by the tumor, such that the nanoparticles are viewed by X-ray scattering imaging, for example spatial harmonic imaging, to detect, image, or diagnose the tumor.

In an embodiment of the composition, the nanoparticles include a metal for example at least one of: silver, copper, gold, mercury, cadmium, zinc, nickel, palladium, platinum, rhodium, mercury, or a combination thereof, and the nanoparticles are determined to be at least about five nm in diameter and less than about 100 nm in diameter.

In an embodiment of the composition, the nanoparticles include a core surrounded by a metal shell with a higher electron density than the core. For example, the core includes carbon or silica.

In an embodiment of the composition, the binding agent is specifically attached to a portion of a surface of the nanoparticles, for example the binding agent is attached using a linker such as an amino acid, a polymer, or a nucleotide, and such that the nanoparticles effectively bind to the tumor and scatters X-rays once irradiated.

In an embodiment of the composition, the nanoparticles include a fullerene or $C_{60}$ Bucky ball, and the binding agent is linked for example to the Bucky ball. In various embodiments of the composition, the binding agent includes at least one selected from the group of: a drug, a protein such as an antibody or a binding protein, a carbohydrate such as a sugar, and a nucleotide sequence. For example, the binding agent includes a monoclonal antibody, a polyclonal, or a portion thereof.

An aspect of the invention provides a method of diagnosing a presence of a tumor in a subject comprising: contacting a tissue with a composition comprising a nanoparticle having at least one binding agent that binds to and/or is suitable for phagocytosis by the tumor; and, detecting the presence of the tumor attached to the nanoparticle using X-ray scatter imaging for example spatial harmonic imaging. In various embodiments of the method, the composition further comprises any of compositions described herein.

In an embodiment of the method, detecting the presence of the tumor includes applying a mathematical operation such as a Fourier transform to detect X-ray scatter measurements or data. In an embodiment of the method, detecting the presence of the tumor is performed using an absorption grid. In an embodiment of the method, the detector includes a camera such as a charge coupled device that detects the presence of the composition and/or nanoparticle.

An aspect of the invention provides a kit for diagnosing a presence of a tumor in a subject comprising: a composition including a nanoparticle having at least one binding agent that binds to and/or is suitable for phagocytosis by the tumor; instructions for use; and a container. In various embodiments of the kit, the composition comprises any of the compositions described herein for detecting or diagnosing the tumor by X-ray scattering imaging including for example at least one of: nanoparticles having at least one binding agent that binds to and/or is suitable for phagocytosis by the tumor; a composition having: a gold nanoparticle, a polymer layer coating the nanoparticle, such that the polymer layer includes for example a polyethylene glycol or a polyelectrolyte such as an anionic poly(acrylic acid) or a cationic poly(allylamine hydrochloride); and, a binding agent that specifically binds a tumor antigen, such that the binding agent is bound to the polymer layer. The kit in an embodiment further includes a receptacle.

The compositions, methods, kits and devices herein show an imaging technique for visualizing cells and/or for the early diagnosis of cancers and tumors (e.g., hepatocellular carcinoma) using surface-modified nanoparticles (having an attached binding agent) and X-ray imaging. The binding agent selectively binds to for example a tumor or cancer cell, and in certain embodiments is an antibody such as a monoclonal antibody, a polyclonal antibody, or a portion thereof. In certain embodiments the monoclonal antibody is a FB50 antibody (Rand et al. 2011 Nano Lett. 11:2678-2683), or a SF25 antibody. See also Takahashi et al., 1988 Cancer Res 48: 6573 and Takahashi et al. U.S. Pat. No. 5,212,085 issued May 18, 1993. Cancerous issues labeled with these electron-dense particles and imaged using spatial harmonic imaging show enhanced X-ray scattering over normal tissues, allowing for effectively differentiation of the cancerous cells containing the nanoparticles from normal non-cancerous cells not containing the nanoparticles. Data show both in vitro and in vivo detection of tumors as small as a few millimeters in size.

Binding Agents

The methods of the present invention use nanoparticles and spatial frequency heterodyne imaging in certain embodiments to image cells or a tissue, and to diagnose or prognose presence or progression of a type of cell or tissue (e.g., cancerous). The nanoparticles in embodiments herein include a binding agent such as least one selected from the group of: a drug, a protein, a carbohydrate, and a nucleotide sequence In certain embodiments, the binding agent is an antibody that is attached or conjugated to the nanoparticle and selectively binds the cells or the tissue, such as a tumor. The term "antibody" as used herein includes whole antibodies and any antigen binding fragment (i.e., "antigen-binding portion") or single chains of these. A naturally occurring "whole" antibody is a glycoprotein including at least two heavy (H) chains and two light (L) chains inter-connected by disulfide bonds.

As used herein, an antibody that "specifically binds to a tumor" refers to an antibody that binds to tumor or tumor antigen. As used herein, an antibody that "specifically binds to a cell" refers to an antibody that binds to a cellular antigen. For example the antibody has a $K_D$ of $5 \times 10^{-9}$ M or less, $2 \times 10^{-9}$ M or less, or $1 \times 10^{-10}$ M or less. For example, the antibody is a monoclonal antibody or a polyclonal antibody. The terms "monoclonal antibody" or "monoclonal antibody composition" as used herein refer to a preparation of antibody molecules of single molecular composition. A monoclonal antibody composition displays a single binding specificity and affinity for a target such as cells or a particular cellular epitope. The antibody is for example an IgM, IgE, IgG such as IgG1 or IgG4.

Also useful for systems, method and kits herein is an antibody that is a recombinant antibody. The term "recombinant human antibody", as used herein, includes all antibodies that are prepared, expressed, created or isolated by recombinant means, such as antibodies isolated from an animal (e.g., a mouse). Mammalian host cells for expressing the recombinant antibodies used in the methods herein include for example Chinese Hamster Ovary (CHO cells) including dhfr⁻ CHO cells, described Urlaub and Chasin, Proc. Natl. Acad. Sci. USA 77:4216-4220, 1980 used with a DHFR selectable marker, e.g., as described in R. J. Kaufman and P. A. Sharp, 1982 Mol. Biol. 159:601-621, NS0 myeloma cells, COS cells and SP2 cells. In particular, for use with NS0 myeloma cells, another expression system is the GS gene expression system shown in WO 87/04462, WO 89/01036 and EP 338, 841. To produce antibodies, expression vectors encoding antibody genes are introduced into mammalian host cells, and the host cells are cultured for a period of time sufficient to allow expression of the antibody in the host cells or secretion of the antibody into the culture medium in which the host cells are grown. Antibodies are recovered from the culture medium using standard protein purification methods.

Standard assays to evaluate the binding ability of the antibodies toward the target of various species are known in the art, including for example, ELISAs, western blots and RIAs. The binding kinetics (e.g., binding affinity) of the antibodies also can be assessed by standard assays known in the art, such as by Biacore analysis.

General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such as the intact protein or a portion thereof containing an epitope (e.g., HCC or CD44), effective to produce an immune response. An exemplary protocol is as follows. The animal is subcutaneously injected in the back with 100 micrograms to 100 milligrams of antigen, dependent on the size of the animal, followed three weeks later with an intraperitoneal injection of 100 micrograms to 100 milligrams of immunogen with adjuvant dependent on the size of the animal, for example Freund's complete adjuvant. Additional intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing a cellular antigen used for immunization.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Pharmaceutical Compositions

An aspect of the present invention provides pharmaceutical compositions that include a nanoparticle having at least one of a polymer layer and a binding agent. In certain embodiments, the composition comprises a plurality of nanoparticles that are administered to cells, a tissue, or a subject. The nanoparticles in certain embodiments undergo cellular uptake by for example phagocytosis and endocytosis. In various embodiments, the nanoparticles are conjugated to a binding agent that binds to a molecular antigen of cell or a tissue. In related embodiments, the pharmaceutical composition is formulated sufficiently pure for administration to a subject, e.g., a human, a mouse, a rat, a dog, a cat, and a cow. The pharmaceutical composition is administered for example to an abdomen or a vascular system.

In certain embodiments, the pharmaceutical composition further includes at least one therapeutic agent selected from the group consisting of growth factors, anti-inflammatory agents, vasopressor agents including but not limited to nitric oxide and calcium channel blockers, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGFs), IGF binding proteins (IGFBPs), epidermal growth factor (EGF), platelet derived growth factor (PDGF), neu differentiation factor (NDF), hepatocyte growth factor (HGF), vascular endothelial growth factor (VEGF), heparin-binding EGF (HBEGF), thrombospondins, von Willebrand Factor-C, heparin and heparin sulfates, and hyaluronic acid. See Toole et al. U.S. Pat. No. 5,902,795 issued May 11, 1999, which is incorporated by reference herein in its entirety.

The therapeutic agent in various embodiments includes an anti-cancer or anti-tumor agent selected from the group of: alkylating agents, such as mechlorethamine, cyclophosphamide, melphalan, uracil mustard, chlorambucil, busulfan, carmustine, lomustine, semustine, streptozoticin, and decrabazine; antimetabolites, such as methotrexate, fluorouracil, fluorodeoxyuridine, cytarabine, azarabine, idoxuridine, mercaptopurine, azathioprine, thioguanine, and adenine arabinoside; natural product derivatives, such as irinotecan hydrochloride, vinblastine, vincristine, dactinomycin, daunorubicin, doxorubicin, mithramycin, taxanes (e.g., paclitaxel) bleomycin, etoposide, teniposide, and mitomycin C; and miscellaneous agents, such as hydroxyurea, procarbezine, mititane, and cisplatinum. See Brown et al. U.S. publication number 20050267069 published Dec. 1, 2005, which is incorporated by reference herein in its entirety.

In other embodiments, the therapeutic agent is a compound, composition, biological or the like that potentiates, stabilizes or synergizes the effects of another molecule or compound on a cell or tissue. In some embodiments, the drug includes without limitation anti-tumor, antiviral, antibacterial, anti-mycobacterial, anti-fungal, anti-proliferative or anti-apoptotic agents. Drugs that are included in the compositions of the invention are well known in the art. See for example, Goodman & Gilman's The Pharmacological Basis of Therapeutics, 9th Ed., Hardman, et al., eds., McGraw-Hill, 1996; and Goodman & Gilman's The Pharmacological Basis of Therapeutics, 12th Ed., Hardman, et al., eds., McGraw-Hill, 2010, the contents of which are herein incorporated by reference herein.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences $20^{th}$ Edition by Gennaro, Mack Publishing, Easton, Pa., 2003 provides various carriers used in formulating pharmaceutical compositions and known techniques for the preparation thereof. Some examples of materials which can serve as pharmaceutically acceptable carriers include, but are not limited to, sugars such as glucose and sucrose; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, the choice of agents and non-irritating concentrations to be determined according to the judgment of the formulator.

Therapeutically Effective Dose

Methods provided herein involves administering a pharmaceutical composition to cells or to a subject, for example, administering a therapeutically effective amount of a pharmaceutical composition having nanoparticles having at least one of a polymer layer and a binding agent. The pharmaceutical composition in certain embodiments optionally further includes a therapeutic agent in such amounts and for such time as is necessary to achieve the desired result.

The compositions, according to the method of the present invention, are administered using any amount and any route of administration effective for contacting cells or a subject. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., intermediate or advanced stage of a disease condition; age, weight and gender of the patient; diet, time and frequency of administration; route of administration; drug combinations; reaction sensitivities; and tolerance/response to therapy. Long acting pharmaceutical compositions might be administered hourly, twice hourly, every three to four hours, daily, twice daily, every three to four days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be diagnosed or to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, as provided herein, usually mice, but also potentially from rats, rabbits, dogs, or pigs. The animal cell model provided herein is also used to achieve a desirable concentration and total dosing range and route of administration. Such information can then be used to determine useful doses and routes for administration in humans.

A therapeutically effective dose refers to that amount of active agent that can be clearly imaged for diagnosis of cells or tissues (e.g., tumors) at a very early stage, or that ameliorates the symptoms or prevents progression of a pathology or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies are used in formulating a range of dosage for human use.

Administration of Pharmaceutical Compositions

As formulated with an appropriate pharmaceutically acceptable carrier in a desired dosage, the pharmaceutical composition provided herein is administered to humans and other mammals topically such as ocularly (as by solutions, ointments, or drops), nasally, bucally, orally, rectally, topically, parenterally, intracisternally, intravaginally, or intraperitoneally.

Injections include intravenous injection, direct or parental injection into the tissues (e.g., cancerous and non-cancerous), or injection into the external layers of the tissue or adjacent tissues, such as for example injection into the peritoneal cavity, stomach, liver, breast, leg, or lung.

The pharmaceutical composition in various embodiments is administered with inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous routes of administration are achieved with aqueous drops, a mist, an emulsion, or a cream. Administration may be diagnostic, prognostic, therapeutic or it may be prophylactic. The invention includes delivery devices, surgical devices, audiological devices or products which contain disclosed compositions (e.g., gauze bandages or strips), and methods of making or using such devices or products. These devices may be coated with, impregnated with, bonded to or otherwise treated with a composition as described herein.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For the purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of the invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

A portion of the invention is provided in a publication in the Journal Nano Letters and is entitled "Nanomaterials for X-ray Imaging: Gold Nanoparticle-Enhancement of X-ray Scatter Imaging of Hepatocellular Carcinoma" by Danielle Rand, Vivian Ortiz, Yanan Liu, Zoltan Derdak, Jack R. Wands, Milan Tatiček, and Christoph Rose-Petruck (Rand et al. 2011 Nano Lett. 11: 2678-2683), which is hereby incorporated by reference in its entirety.

The following examples and claims are illustrative only and not intended to be further limiting. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference in their entireties. A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. Therefore, it is contemplated to cover the present embodiments of the invention and any and all modifications, variations, or equivalents that fall within the true spirit and scope of the basic underlying principles disclosed and claimed herein.

EXAMPLES

Example 1

Materials

Chemicals were purchased from Sigma-Aldrich Inc. (St. Louis, Mo.) unless otherwise specified. Uncoated gold nanoparticles (ten nm and 50 nm) stabilized in citrate buffer were purchased from British Biocell International (Cardiff, UK): 10 nm gold nanoparticles were BBI catalog #EMGC10, batch #15683; and 50 nm gold nanoparticles were BBI catalog #EMGC50, batch #15693.

Example 2

Layer-by-Layer Coating of Nanoparticles

Stock solutions of poly(acrylic acid) (PAA) and poly(allylamine hydrochloride) (PAH) were prepared (10 mg/mL PAA or PAH in one millimolar (mM) aqueous sodium chloride solution). Unpurified one milliliter (mL) aliquots of ten nm gold nanoparticles or of 50 nm gold nanoparticles were mixed with 100 microliters (μL) of 1 mM sodium chloride and 200 μL of PAA stock solution. The mixture was incubated for 30 minutes. Excess polymer in the supernatant was removed by centrifugation. Anionic poly(acrylic acid) (PAA) was deposited on the gold nanoparticles, resulting in a gold nanoparticle being coated with carboxylic acid groups located on the nanoparticle surface (FIG. 1; AU-PAA nanoparticle).

The PAA-coated nanoparticle were re-suspended in phosphate buffered saline (PBS). The PAA encapsulated gold nanoparticles (one mL aliquots) were then mixed with 100 μL of 1 mM sodium chloride and 200 μL of cationic poly(allylamine hydrochloride) stock solution for 30 minutes. The electrostatic interaction between the oppositely charged PAA and PAH polymer layers yielded a layer-by-layer coating of the PAA and PAH polyelectrolytes on the surface of the nanoparticles.

The mixture was then centrifuged to remove excess polymer in the supernatant. The resulting gold nanoparticles were coated with an inner layer of PAA polymer and an outer layer of PAH polymer. Solutions containing the PAA-PAH coated gold nanoparticles were stored at room temperature.

Example 3

Preparation of FOCUS Cells

FOCUS cells were cultured and maintained at 37° C. (5% $CO_2$) in Eagle's Minimum Essential Medium (EMEM) supplemented with 10% fetal bovine serum, 1% penicillin/streptomycin and 1% L-glutamine. Cells were grown to confluence and formed a monolayer. Trypsin was added to detach the FOCUS cells, which were re-suspended in serum-free EMEM.

Example 4

Incubation of FOCUS Cells with Coated Nanoparticles

To prepare samples for X-ray scatter imaging, cell pellet samples containing approximately $10^7$ FOCUS cells were incubated in vials with nanoparticle solutions containing either ten nm PAA-PAH coated gold nanoparticles, or 50 nm PAA-PAH coated gold nanoparticles. Control cell pellet samples were incubated with either no gold, or with ten nm uncoated gold nanoparticles only, viz., no PAA-PAH coating. The number of FOCUS cells in the cell pellet samples was chosen to model the size of a small tumor having a diameter of a few millimeters.

After each incubation, the cells were collected, washed and imaged. The approximate amount of gold nanoparticles contained in each incubation with the cell pellet samples was measured in Example 8 by spectrometric methods.

Example 5

Spatial frequency Heterodyne Imaging of the FOCUS Cells and Nanoparticles

Spatial frequency heterodyne imaging was used to image samples of FOCUS cell pellets contacted with gold nanoparticles. The spatial frequency heterodyne imaging system shown in FIG. 2 directed X-ray radiation to an absorption grid and a sample, and then detected the X-rays scattered by the sample to using a detector and Fourier transformation (Stein, A. F. et al. 2010 Opt. Express 18: 13271-13278; Wen, H. et al. 2009 Radiology 251: 910-918; and Wen, H. et al. 2008 IEEE Trans Med Imaging 27: 997-1002). A vial holder positioned the vials containing the cell pellets-gold nanoparticles.

The X-ray scatter measurements were obtained with a micro-focus X-ray tube (Trufocus Corporation, model: TFX-3110EW) with a tungsten anode. The tube was operated at an electrical power of 20 watts (W), producing a maximum voltage of 95.6 kilovolts (kV). High voltages reduced the exposure times, and were observed to be better suited for in vivo applications, as imaging a tissue in a subject required large penetration depths. The distance between the source and camera was 1.6 meters (m), and the sample was placed at a distance halfway (0.8 m) between the source and camera to enhance resolution (Wen, H. et al. 2009 Radiology 251: 910-918).

The absorption grid was stainless steel with a pitch of 50 micrometer (μm), and was purchased from Small Parts, Inc. (Seattle, Wash.). The grid was positioned directly in front of the vials containing the cell pellet samples and the gold nanoparticles. The images were acquired with an X-ray CCD camera (Princeton Instruments, Model Quad-RO 4096). The total exposure time for each image was 180 seconds.

Example 6

Fourier Transformation of Images

Figure 3:
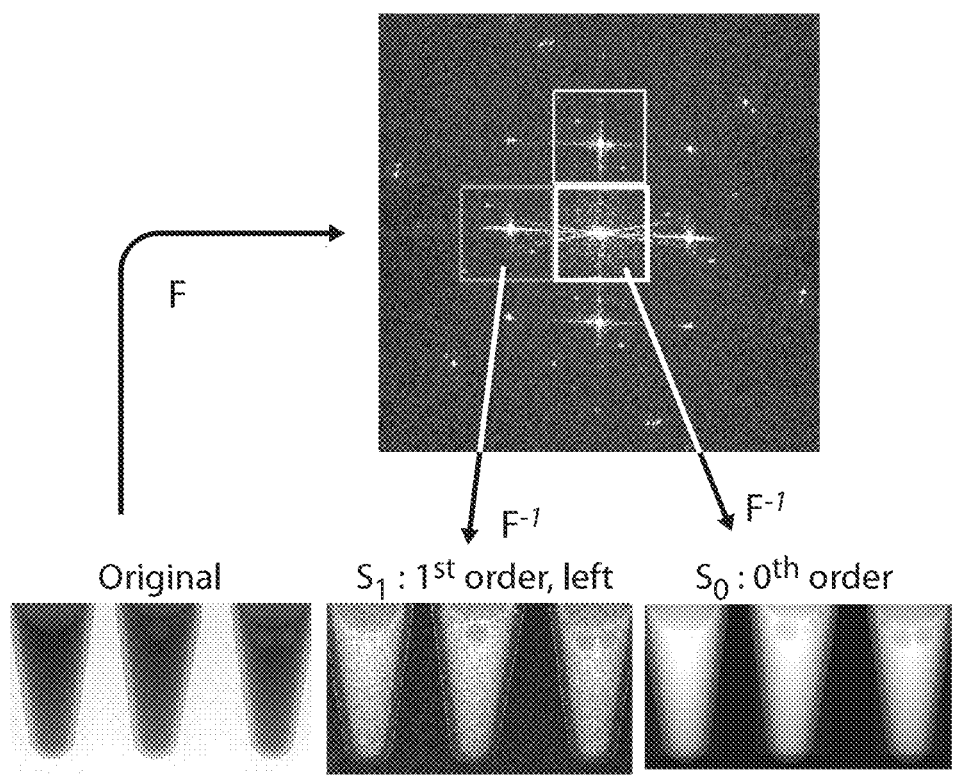
FIG. 3 is a set of visible light images and X-ray scatter images after Fourier transformation of scattered X-radiation of a sample obtained by the imaging system shown in FIG. 2. A beam of X-radiation was directed through an absorption grid and sample in a vial, and was detected using an CCD. The original image (F) is shown in the lower left of FIG. 3. A Fourier transformation was performed resulting in an image in the spatial frequency domain. Different peaks in the spatial frequency image contained different information regarding scattering of incident x-radiation by the sample. Selecting an area around a specific peak in the convolution and Fourier back-transforming this area returns the logarithm of the scattered intensities to real space and gives a processed image that contains anisotropic information regarding scattering of the incident X-rays by the sample. The area surrounding the central $0^{th}$-order peak (F$^{-1}$; S0: $0^{th}$ order.
Figure 4A:
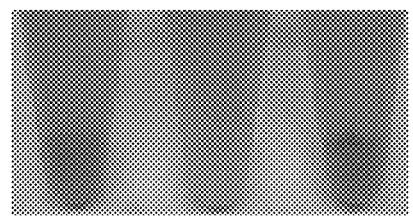
FIG. 4 panels A-D are a set of images showing vials with cell pellets containing approximately 10$^7$ FOCUS cells (Friendship of China and United States; a human hepatocellular carcinoma cell line; He, L. et al. 1984 In Vitro 20(6): 493-504) labeled with PAA-PAH coated gold nanoparticles having a diameter of 10 nm (right vial in each panel) or 50 nm (left vial in each panel). Control cells were not contacted with gold nanoparticles (center vial in each panel). Top boxes and bottom boxes in each of FIG. 4 panels B-D outline areas selected for intensity profiles of the supernatant and pellet, respectively. Data show improved sensitivity and clarity for spatial harmonic images of coated nanoparticles compared to absorbance images.
Figure 4B:
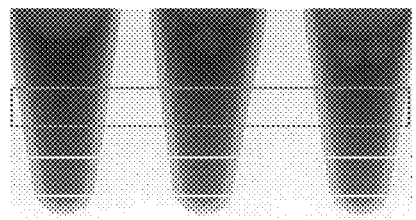
Figure 4C:
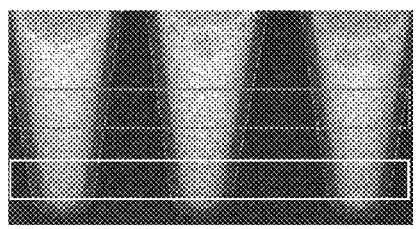
Figure 4D:
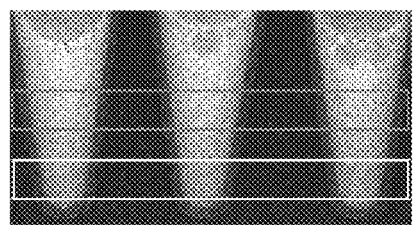

Fourier transformation was then performed on the original images (FIG. 3 bottom left image; F, Original). The Fourier transformation converted the product of X-ray scatter transmittances of the sample and the grid into a convolution in the spatial frequency domain (see FIG. 3). The grid, a periodic structure, produced a series of peaks in this convolution. Each peak produced by the grid was "surrounded" by the spatial frequency spectrum of the sample.

Selecting an area around a specific peak in the convolution and Fourier back-transforming this area yielded a logarithm of the scattered intensities to real space and provided a processed image that contained anisotropic information about the scattering of the incident X-rays by the sample. The area surrounding the central $0^{th}$-order peak (FIG. 3 bottom right image; $F^{-1}$, $S_0$: $0^{th}$ order) corresponded to the original X-ray absorption image without scatter, which was then used for normalizing the images. The X-ray absorption image without scatter was subtracted from the higher order images to remove absorption features that distort clear visualization of the cell pellet samples.

The area around the $1^{st}$-order peak to the immediate left of the $0^{th}$-order peak (FIG. 3 bottom center image; $F^{-1}$, $S_1$: $1^{St}$ order, left) corresponded to scattering in the x-direction, and therefore produced a processed "left $1^{st}$-order" scatter image upon Fourier back-transformation and normalization. Further, the area around the $1^{st}$-order peak immediately above the $0^{th}$-order peak (FIG. 3 top image top right box) corresponded to scattering in the y-direction, and therefore producing a processed "upper $1^{st}$-order" scatter image upon Fourier back-transformation and normalization. Thus, the original X-ray image obtained yielded two Fourier transformation processed images. A processed image resulting from X-radiation scattered horizontally (FIG. 3 bottom center image; $F^{-1}$, $S_1$: $1^{st}$ order), and the processed image from x-radiation scattered vertically (FIG. 3 top image top right box). Both of these $1^{st}$ order images produced identical scatter signals because of the isotropic scattering of the spherical nanoparticles.

Example 7

Calculation of Scatter Signals and Enhancement Factors

The scattering signal (S) for each processed image was calculated according to the following equation:

$$S = -\log\left(\frac{I_1/G_1}{I_0/G_0}\right)$$

such that $I_1$ and $I_0$ were the detected X-ray signals with sample in the $1^{st}$ and $0^{th}$ order, respectively. In the equation above, $G_1$ and $G_0$ were the detected X-ray signals without sample in the $1^{st}$ and $0^{th}$ order, respectively. The signal S was calculated for each vial in the area that contains the cell pellet ($S_{cells}$) and the area of the supernatant ($S_{super}$). Precautions were taken to avoid detecting any signal from the walls of the vials. The normalized scattering signal ($S_{norm}$) for each cell pellet was calculated by dividing the signal measured in the area containing the cell pellet ($S_{cells}$) by the signal measured in the area of the supernatant ($S_{super}$) as shown in the equation below:

$$S_{norm} = \frac{S_{cells}}{S_{super}}$$

The normalized scattering signal was then compared to the absorbance measured in the original absorption X-ray images. The absorbance was calculated using the following equation:

$$A = -\log\left(\frac{I_{sample}}{I_{flat\ field}}\right)$$

such that, $I_{sample}$ was the detected X-ray intensity with a sample vial and $I_{flat\ field}$ was the detected X-ray intensity without a sample vial. The absorbance was calculated for each vial in the area containing the cell pellet ($A_{cells}$) and in the area of the supernatant ($A_{super}$), respectively. The normalized absorbance signal ($A_{norm}$) measured for each pellet in the absorption images was calculated by dividing the signal measured in the area containing the cell pellet ($A_{cells}$) by the signal measured in the area of the supernatant ($A_{super}$) using the equation shown below:

$$A_{norm} = \frac{A_{cells}}{A_{super}}$$

The scattering signal ($S_{norm}$) was compared to the absorption signal ($A_{norm}$) measured in the absorption images by calculating an enhancement factor as shown in an equation below:

$$\text{Enhancement factor} = \frac{S_{norm}}{A_{norm}}$$

Example 8

ICP-AES Analysis of Gold in Cell Pellet Samples

The signal enhancement in the processed X-ray images due to increased scattering by the gold nanoparticles was normalized by spectrophotometric techniques for gold content (mass) in the cells. After the pellets were imaged using X-ray scattering, the amount of gold taken up by the FOCUS cell pellets during incubation was determined using inductively-coupled plasma atomic emission spectroscopy (ICP-AES).

Samples were prepared for ICP-AES analysis by digesting gold and organics with aqua regia (1:3 mixture of $HNO_3$:HCl) followed by dilution in 2% nitric acid. Data from ICP-AES analysis showed that the samples contained four micrograms to eight micrograms (μg), corresponding to several hundred 50 nm nanoparticles per cell and tens of thousands of ten nm nanoparticles per cell (shown in Tables 1 and 2).

Example 9

Images Analysis

FIG. 4 panels A-D are representative photographs (FIG. 4 panel A), absorption images (FIG. 4 panel B) and X-ray scatter images (FIG. 4 panels C-D) of vials containing FOCUS cell pellets incubated with either 50 nm PAA-PAH coated gold nanoparticles (FIG. 4 left image in each panel), or ten nm. PAA-PAH coated gold nanoparticles (FIG. 4 right image in each panel). Control samples of FOCUS cell pellets were incubated with no gold nanoparticles (FIG. 4 center image in each panel).

Visual analysis of photographs clearly indicated that samples incubated with PAA-PAH coated gold nanoparticles were labeled with gold, and that control samples incubated with no gold nanoparticles were not labeled (FIG. 4 panel A). Cell pellets containing gold nanoparticles were stained a distinctive brown color. It was observed that for each of the samples the EMEM supernatant located above the cell pellet was naturally pink and showed no presence of gold nanoparticles. No clear labeling of FOCUS cell pellets was observed in images obtained using conventional absorption techniques. For the absorption images, FOCUS cell pellets incubated with gold nanoparticles and the cell pellet samples incubated with no gold nanoparticles were indistinguishable from each other (FIG. 4 panel B). Most important, images obtained by spatial frequency heterodyne imaging showed a signal enhancement in samples incubated with the PAA-PAH coated gold nanoparticles compared to control cells having no nanoparticles because of uptake of the gold nanoparticles into the cell pellets (FIG. 4 panels C-D).

The signal enhancement for spatial frequency heterodyne imaging compared to absorbance imaging was calculated by first obtaining an average intensity profile of the absorbance image at the pellet height ($A_{cells}$), such that the average absorbance intensity varied depending on presence of gold nanoparticle concentration contacting the cells. The absorbance value was normalized using the intensity of the supernatant ($A_{super}$) which was approximately the same for each of the samples irrespective of whether samples contained gold nanoparticles or not. The upper right boxes and two lower boxes shown in FIG. 4 panels B-D outline the areas selected for calculating intensity profiles of the supernatant and pellet, respectively. The intensity values were averaged using the optical data from the outlined areas. Examples herein used a vial holder for positioning the vials containing the cell pellets-gold nanoparticles described above ensured that the average signal intensities were standardized for each image obtained, as absorbance and signal comparisons between the samples were obtained from the same relative positions (having the same thickness) in the vials containing the samples.

Data show that gold nanoparticles not coated with PAA and PAH polyelectrolytes were not effectively uptaken by the FOCUS cell pellets. Data show that less than 25% of the uncoated nanoparticles used for incubation were phagocytosed by the FOCUS cells after the one hour contact with the nanoparticles. Clearly these control cell pellets were observed to have reduced intensity due to the relatively low gold concentrations in each cell (see Table 1).

Coating gold nanoparticles with the PAA-PAH polymer coatings enhanced FOCUS cell pellets cellular uptake (e.g., phagocytosis) of the nanoparticles compared using non-coated control nanoparticles. Layer-by-layer coating of the nanoparticles resulted in increased amount of gold in each cell, and therefore the increased scattering signal observed in the X-ray images obtained (Table 1). Data in Table 1 further show that the FOCUS cells phagocytosed more than twice as many ten nm PAA-PAH coated gold nanoparticles (275,000 nanoparticles) as ten nm uncoated gold nanoparticles (108,000 nanoparticles).

Most important, FOCUS cells phagocytosed twice as much mass of gold per cell of 10 nm PAA-PAH coated gold nanoparticles (2.8±0.4 picograms per cell) and 50 nm PAA-PAH coated gold nanoparticles (2.2±0.3 picograms per cell) compared to uncoated gold nanoparticles (1.2±0.5 picograms per cell). The uptake of the nanoparticles was enhanced by the PAA-PAH coating, as data showed that FOCUS cells phagocytosed an average of approximately 275,000 polyelectrolyte-coated ten nm PAA-PAH gold nanoparticles per cell, compared to approximately 108,000 uncoated ten nm gold nanoparticles per cell (Table 1).

It was observed that FOCUS cell pellets phagocytosed approximately the same amount of PAA-PAH coated nanoparticles irrespective if the nanoparticles were ten nm (2.8±0.4 picograms) or 50 nm (2.2±0.3) in size (Table 1). Without being limited by any particular theory or mechanism of action, it is here envisioned that the total volume of gold nanoparticles incubated with the cells that is an important factor in determining the extent of cellular uptake. Calculation of the percentage volume of the nanoparticles in the cell indicated than only a very small portion of each cell is actually occupied by the coated gold nanoparticles. Data show that the FOCUS cells phagocytosed a cell volume of much less than 0.001% of PAA-PAH polyelectrolyte-coated nm gold nanoparticles: 10 nm PAA-PAH coated gold nanoparticles (0.00063%), 50 nm PAA-PAH coated gold nanoparticles (0.00049%), and uncoated 10 nm gold nanoparticles (0.00025%).

Analysis of the absorption X-ray images further shows that the signal measured for FOCUS cell pellets incubated with PAA-PAH coated gold nanoparticles was 1.2% greater than the signal measured for FOCUS cell pellets incubated without gold nanoparticles (see Table 2). However, of the total number (12) of absorption images taken of FOCUS cell pellets labeled with gold nanoparticles, only 58% (seven) were observed to have exhibit any enhancement due to gold labeling by the nanoparticles. The large standard deviation calculated for absorption techniques illustrates the extent that absorption images are unreliable for imaging cells in vitro, let alone in vivo.

The spatial frequency heterodyne imaging described herein visualized and differentiated between FOCUS cell pellets incubated with PAA-PAH coated gold nanoparticles and control FOCUS cell pellets incubated with no gold nanoparticles. The left 1$^{st}$-order scatter images (FIG. 4 panel C) and upper 1$^{st}$-order scatter images (FIG. 4 panel D) produced using spatial frequency heterodyne imaging were analyzed and used to produce normalized intensity profiles for the cell pellet samples. These calculated normalized profiles corresponded to the logarithm of the intensity of the scattered x-radiation. Without being limited by any particular theory or mechanism of action, it is envisioned that the signal differences between the 1$^{st}$ order images were due to the side interfaces produced by either air in the vials (FIG. 4 panel C) or the bottom interface of the vials (FIG. 4 panel D). Thus the signal differences in the 1$^{st}$-order spatial frequency heterodyne imaging were from anisotropic X-ray scattering at smooth material interfaces.

Analysis of processed spatial frequency heterodyne (X-ray scatter) images and the ICP-AES data in Examples herein shows an average signal enhancement due to gold labeling that ranges from approximately 1.6% to 4.4% (Table 2). Of the X-ray scatter images (24 total images) taken of FOCUS cell pellets labeled with gold nanoparticles, 88% (21 images) showed a signal enhancement when compared to X-ray scatter images of FOCUS pellets containing no gold. Overall, the data herein of processed spatial frequency heterodyne images and ICP-AES show an at least three or at least a five enhancement factor per picogram of gold uptaken by the cell (Table 2).

These data show that for every picogram of gold taken up by a cell, the signal observed in the processed scatter images was enhanced by an average of 3.6% and 5.7% (Table 2; replicate 1 and replicate 2, respectively). It was observed that each cell contained an average of about three picograms of polyelectrolyte-coated gold nanoparticles (Table 1), resulting in a potential signal enhancement due to gold labeling of approximately 11% to approximately 17% in logarithm scale (Table 2).

Example 10

Model of In Vivo Imaging Using Nanoparticles and Spatial Frequency Heterodyne Imaging Examples herein show development of an X-ray scatter imaging system for in vivo imaging of cells and tissues. The in vivo model utilized signal enhancement produced by gold nanoparticle labeling such that the signal enhancement would correspond to visualizing cells and structures beneath many layers of tissue.

Figure 2:
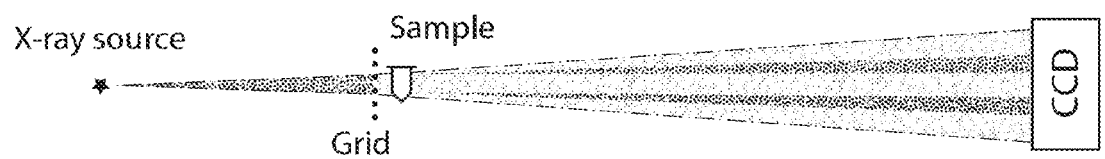
FIG. 2 is a drawing of the X-ray imaging system used in examples herein. An X-ray source directs electromagnetic radiation to an absorption grid that is a periodic structure positioned in the radiation propagation direction and positioned proximal to a sample and a charged-coupled device (CCD). The grid scatters the directed radiation to the sample positioned in a container or vial. The X-ray radiation passes through the grid and the sample respectively, and is then detected using the CCD.

Spatial frequency heterodyne imaging was performed as described in FIG. 2 for a cell pellet sample incubated with 50 nm PAA-PAH coated gold nanoparticles, in which X-ray radiation progressed through one centimeter of water prior to reaching the cell pellets previously contacted with nanoparticles. X-ray radiation traversing one centimeter of water positioned above the cell pellet-gold nanoparticles was chosen to imitate closely a thickness of tissue which X-ray radiation delivered to a patient's skin might traverse at the point of entry into the patient.

Water and liver tissues have similar radiological densities, in fact the electron densities of water and liver tissues differ by less than 5% (Yang, M. et al. 2010 Physics in Medicine and Biology 55: 1343-1362). X-ray scatter imaging an additional traversal through one centimeter of water resulted in the detection of gold-labeled FOCUS cell pellets. Data show that normalized signal intensities in the scatter images increased by 1.8±0.5% for cells incubated with gold nanoparticles compared to a control cell pellet incubated with no gold nanoparticles.

Example 11

Imaging Cells Using Antibody-conjugated Nanoparticles

Nanoparticles linked to HCC-specific antibodies were prepared to determine whether such compositions would be useful as X-ray visible immunolabels, for in vivo detection and X-ray imaging of HCC tumors in a murine mouse model.

The FB50 monoclonal antibody was generated by cellular immunization of mice with FOCUS HCC cells. The FB50 antibody specifically binds and targets FOCUS cells, and the antibody is localized intracellularly. To reduce nonspecific uptake of the gold nanoparticles by the other types of tissue, the nanoparticle surface was coated with a polyethylene glycol (PEG). Without being limited by any particular theory or mechanism of action, it is here envisioned that PEG prevented the non-specific adsorption of the proteins onto the nanoparticle surface, allowing for longer circulation times in vivo and enhanced accumulation of the nanoparticle specifically in the liver of the subject.

Bi-functional PEG (HS-PEG-COOH) was added to the nanoparticle, for facile attachment to the nanoparticle surface. Bio-conjugation of the gold nanoparticles to the FB50 antibody was performed using techniques involving EDC/NHS cross-linking chemistry. The bio-conjugation involved linking the carboxylic acid groups on the PEG coating around the nanoparticles to amine groups present on the FB50 antibody (See FIG. 5). Dynamic light scattering techniques showed that each of the steps of producing the PEG coated the gold nanoparticles and the conjugated FB50 antibody resulted in increases to the diameter of the 50 nm gold nanoparticles (FIG. 6 panel A). Specifically data showed that the uncoated 50 nm gold particles had a diameter of 71.3±10.0 nm, that the PEG-coated 50 nm gold nanoparticles had a diameter of 81.8±12.1 nm, and that the PEG-coated FB50 antibody conjugated 50 nm gold nanoparticles had a diameter of 93.9±18.3 nm (FIG. 6 panel A). Without being limited by any particular theory or mechanism of action, it is here envisioned that PEG coated on the nanoparticle surface prevented the non-specific adsorption of the antibody-conjugated nanoparticles to cells not expressing HCC, allowing for longer circulation times in vivo and enhanced accumulation of the nanoparticle specifically in the liver of the subject.

Cellular uptake by FOCUS cells pellets and by NIH/3T3 cell pellets of the PEG coated gold nanoparticles or the PEG coated FB50 conjugated ten nm gold nanoparticles was measured (FIG. 6 panel B). The specificity of FB50 antibody was evaluated by using as a negative control the NIH/3T3 fibroblasts, which do not express HCC. An anti-Murutucu tropical virus (MUK) antibody was also used as an additional negative control antibody for the FOCUS cells, as the MUK antibody does not specifically bind HCC (FIG. 6 panel B).

Data show that at least thirty fold more of the PEG-coated FB50 antibody conjugated ten nm gold nanoparticles were taken into the FOCUS cell pellets compared to the NIH/3T3 cell pellets. Further, little or no PEG-coated MUK antibody conjugated gold nanoparticles were transported into the FOCUS cell or the NIH/3T3 cells. Thus, the PEG-coated FB50 antibody conjugated ten nm gold nanoparticles specifically bound to the HCC antigen and enhanced cellular uptake of the nanoparticles into the FOCUS cells.

Example 12

In Vivo Imaging of Livers

Examples herein used the PEG/FB50 antibody conjugated nanoparticles were tested in an in vivo a murine mouse model. Mice were injected twice over a 24 hour period into the tail vein with 50 nm PEG/FB50 antibody conjugated gold nanoparticles, or saline as a negative control. Subjects were sacrificed 48 hours after the first injection, and were fixed in formaldehyde and imaged in the spatial frequency heterodyne imaging system (FIG. 2) and imaging was performed in situ. Without being limited by any particular theory or mechanism of action, it is envisioned that injected nanoparticles that were not conjugated to the targeting/binding agent FB50 antibody such as the Au-PEG nanoparticles (shown in FIG. 4) concentrated mainly in the liver due to the high phagocytic activity of the Kuppfer cells located in that tissue. In vivo spatial frequency heterodyne imaging was performed in the area of the liver of each subject.

In situ imaging showed that 80% of livers in subjects injected with PEG/FB50 antibody conjugated gold nanoparticles (FIG. 7 panel A right column bottom row) exhibited a brighter normalized scatter signal than livers from subjects injected with the saline control (FIG. 7 panel A right column top row).

Livers were excised from subjects and spatial frequency heterodyne imaging system was performed. It was observed that subjects injected with PEG/FB50 antibody conjugated gold nanoparticles also clearly showed enhanced signal enhancement of the liver compared to spatial frequency heterodyne images of livers from control subjects injected with saline only (FIG. 7 panel B). The spatial frequency heterodyne imaging was also performed in situ for spleens, kidneys and lungs from subjects, and the liver was the primary organ to show significant signal enhancement with an average enhancement of 23.0±14.1%. Enhanced signal enhancements were observed in both absorption images (FIG. 7 panel B left images) and spatial frequency heterodyne imaging (FIG. 7 panel B right images). A greater than a factor of ten signal enhancement was calculated in the scatter images compared to the absorption images. Thus, spatial frequency heterodyne imaging effectively visualized in vivo the size and contours of in vivo organs and greatly outperformed the results obtained by absorption imaging.

Example 13

In Vivo Imaging of Tissues in the Body

Nanoparticles (metal nanoparticles, metal oxide nanoparticles, and MRI agent nanoparticles) are prepared for in vivo administering and imaging of tissues including muscle, bone, cartilage, skin, and blood vessels.

The nanoparticles are contacted with a polymer such that a polymer layer coated the nanoparticles. The polymer layer provides the nanoparticles with a hydrophobic barrier that enhances non-specific cellular uptake. Alternatively, nanoparticles are constructed with both a polymer and a binding agent such that the binding agent extends from the nanoparticle to specifically bind to molecular antigens present on and in cells and tissues.

The nanoparticles described herein are stable at a range of storage temperatures (e.g., room temperature and below freezing) and are non-toxic to subjects. The nanoparticles are formulated into compositions and injected into subjects for imaging.

Absorption imaging and spatial frequency heterodyne imaging are performed in vivo by directing X-ray radiation to tissues of subjects injected with nanoparticles. Deflection of incident X-rays from the primary beam direction are detected in Examples herein by placing an absorption grid between the sample and the X-ray source. Fourier transformations are performed on the original X-ray scatter images to obtain processed images that analyzed by a blind panel of doctors to allow for histological information of the tissues.

The samples of the tissues are then excised, fixed and/or decalcified. Histopathology slides for each tissue are prepared, and multiple images are acquired using a standard microscope and an image analysis software. The panel of doctors then uses the images obtained from the histological slides to identify the type and histological condition of each of the tissues. Data analyses are performed (e.g., sensitivity and specificity) to compare the results obtained from each of the absorption imaging, spatial frequency heterodyne imaging, and the actual histological analysis. Data show that spatial frequency heterodyne imaging using metal nanoparticles, metal oxide nanoparticles, and MRI agent nanoparticles is much more sensitive in imaging and differentiating tissue than absorption imaging. Most important, the spatial frequency heterodyne imaging of tissues injected with the nanoparticles is as effective in diagnosing tissue conditions as actual histological analysis.

What is claimed is:

1. A method of imaging cells or a target tissue in a sample, the method comprising:
    contacting the cells or the target tissue with a nanoparticle composition comprising nanoparticles that bind to or are phagocytosed by the cells or the target tissue, irradiating the sample with an X-ray beam, and
    imaging the cells or tissue by X-ray scatter imaging such that presence of the nanoparticles in nanoparticle-bearing cells or the target tissue improves image clarity, sensitivity and visibility of the cells or target tissue effectively enabling in situ detection of a tumor a few millimeters in size in the x-ray scatter image of an organ or tissue.

2. The method according to claim 1, further comprising prior to contacting the nanoparticle composition, constructing the nanoparticles with at least one material selected from the group consisting of: a metal, a metal oxide, and an organic material.

3. The method according to claim 1, further comprising prior to contacting, constructing the nanoparticles with a magnetic resonance imaging agent thereby enabling MRI imaging of the target tissue imaged by X-ray scatter imaging.

4. The method according to claim 1, wherein the nanoparticles include a polymer layer that comprises at least one of: a polyethylene glycol, a polyelectrolyte, an anionic polymer, and a cationic polymer.

5. The method according to claim 1, further comprising prior to contacting, constructing the nanoparticle with at least one metal selected from the group consisting of: silver, copper, gold, cadmium, zinc, nickel, palladium, platinum, rhodium, platinum, manganese, gadolinium, dysprosium, tantalum, titanium, and iron.

6. The method according to 1, wherein irradiating the sample comprises locating or inserting an absorption grid adjacent to the sample between an X-ray source and a detector.

7. The method according to claim 1, wherein detection of the tumor is performed by spatial frequency heterodyne imaging.

8. The method according to claim 1, wherein the nanoparticles include a binding agent selected from the group consisting of: a drug, a protein, a carbohydrate, a nucleotide sequence and a combination thereof.

9. The method according to claim 1, wherein the tissue comprises a plurality of cells selected from the group consisting of: cancerous, non-cancerous, epithelial, hematopoietic, stem, spleen, kidney, pancreas, prostate, liver, neuron, breast, glial, muscle, sperm, heart, lung, ocular, brain, bone marrow, fetal, blood, leukocyte, lymphocyte, and a combination thereof.

10. The method according to claim 8, wherein the protein is an antibody selected from the group consisting of: a monoclonal antibody, a polyclonal antibody, a single-chain antibody (scFv); a recombinant heavy-chain-only antibody (VHH); an Fv; a Fab; a Fab'; and a $F(ab')_2$.

11. The method according to claim 10, wherein the monoclonal antibody specifically binds a tumor antigen selected from the group consisting of: aspartyl (asparaginyl)-β-hydroxylase, alphafetoprotein, carcinoembryonic antigen (CA), CA-125, mucin 1, epithelial tumor antigen, tyrosinase, melanoma-associated antigen, tumor protein 53, human chorionic gonadotropin, vimentin, CD34, desmin, prostate specific antigen, and glial fibrillary acidic protein.

12. The method according to claim 10, wherein the monoclonal antibody comprises all or a functional portion thereof of FB50 antibody, or SF25 antibody.

13. The method according to claim 1, further comprising detecting a tumor in the cells or the tissue revealed by the scatter-imaging, wherein the tumor is selected from the group consisting of: melanoma; colon carcinoma; pancreatic; lymphoma; glioma; lung; esophagus; mammary; prostate; head; neck; ovarian; stomach; kidney; liver; and hepatocellular carcinoma.

14. The method according to claim 13, wherein the nanoparticles have been constructed to target and bind to the tumor.

15. The method according to claim 1, wherein the nanoparticles include a core portion and a shell portion.

16. The method according to claim 15, wherein the core and shell have different electron densities.

* * * * *